(12) United States Patent
Miller et al.

(10) Patent No.: US 7,274,015 B2
(45) Date of Patent: Sep. 25, 2007

(54) CAPACITIVE DISCHARGE PLASMA ION SOURCE

(75) Inventors: Raanan A. Miller, Brookline, MA (US); Erkinjon G. Nazarov, Lexington, MA (US); Evgeny Krylov, Las Cruces, NM (US); Gary A. Eiceman, Las Cruces, NM (US); Lawrence A. Kaufman, Boston, MA (US)

(73) Assignee: Sionex Corporation, Waltham, MA (US)

( * ) Notice: Subject to any disclaimer, the term of this patent is extended or adjusted under 35 U.S.C. 154(b) by 666 days.

(21) Appl. No.: 10/215,251

(22) Filed: Aug. 7, 2002

(65) Prior Publication Data

US 2003/0070913 A1 Apr. 17, 2003

Related U.S. Application Data

(60) Provisional application No. 60/310,902, filed on Aug. 8, 2001, provisional application No. 60/335,219, filed on Oct. 25, 2001, provisional application No. 60/340,815, filed on Dec. 12, 2001, provisional application No. 60/388,052, filed on Jun. 12, 2002.

(51) Int. Cl.
*B01D 59/44* (2006.01)
(52) U.S. Cl. .................................. 250/288; 250/286
(58) Field of Classification Search ................ 250/288, 250/286, 423 R
See application file for complete search history.

(56) References Cited

U.S. PATENT DOCUMENTS

| | | | |
|---|---|---|---|
| 2,615,135 A | 10/1952 | Glenn, Jr. | |
| 2,818,507 A | 12/1957 | Britten | |
| 2,919,348 A | 12/1959 | Bierman | |
| 3,511,986 A | 5/1970 | Llewellyn | |
| 3,619,605 A | 11/1971 | Cook et al. | ............. 315/111.21 |
| 3,621,240 A | 11/1971 | Cohen et al. | ........... 315/111.21 |
| 3,648,046 A | 3/1972 | Denison et al. | ............. 250/396 |
| 3,931,589 A | 1/1976 | Aisenberg et al. | ...... 315/111.21 |

(Continued)

FOREIGN PATENT DOCUMENTS

SU 966583 10/1982

(Continued)

OTHER PUBLICATIONS

Guevremont, R., et al., "Atmospheric Pressure Ion Focusing in A High-Field Asymmetric Waveform Ion Mobility Spectrometer," *Review of Scientific Instruments*, 70(2):1370-1383 (1999).

(Continued)

*Primary Examiner*—Douglas W. Owens
*Assistant Examiner*—Jimmy Vu
(74) *Attorney, Agent, or Firm*—Fish & Neave IP Group Ropes & Gray LLP

(57) ABSTRACT

In a system for chemical analysis, an RF-driven plasma ionization device including a pair of spaced-apart and plasma-isolated electrodes, the electrodes are connected to a power source wherein the electrodes act as plates of a capacitor of a resonant circuit, the gas electrically discharges and creates a plasma of both positive and negative ions, and the voltage is applied as a continuous alternating waveform or as a series of pulses, such as a packet waveform.

36 Claims, 26 Drawing Sheets

U.S. PATENT DOCUMENTS

| | | | |
|---|---|---|---|
| 4,019,989 A | 4/1977 | Hazewindus et al. | 250/286 |
| 4,025,818 A | 5/1977 | Giguere et al. | 315/111.21 |
| 4,136,280 A | 1/1979 | Hunt et al. | 250/286 |
| 4,163,151 A | 7/1979 | Bayless et al. | 250/287 |
| 4,167,668 A | 9/1979 | Mouriér | 250/292 |
| 4,201,921 A * | 5/1980 | McCorkle | 378/122 |
| 4,315,153 A | 2/1982 | Vahrenkamp | 250/288 |
| 4,517,462 A | 5/1985 | Boyer et al. | 250/286 |
| 4,577,461 A * | 3/1986 | Cann | 60/203.1 |
| 4,761,545 A | 8/1988 | Marshall et al. | 250/288 |
| 4,885,500 A | 12/1989 | Hansen et al. | 250/292 |
| 4,931,640 A | 6/1990 | Marshall et al. | 250/292 |
| 5,019,706 A | 5/1991 | Allemann et al. | 250/293 |
| 5,047,723 A | 9/1991 | Puumalainen | 250/286 |
| 5,144,127 A | 9/1992 | Williams et al. | 250/286 |
| 5,218,203 A | 6/1993 | Eisele et al. | 250/287 |
| 5,298,745 A | 3/1994 | Kernan et al. | 250/292 |
| 5,373,157 A | 12/1994 | Hiroki et al. | 250/288 |
| 5,420,424 A | 5/1995 | Carnahan et al. | 250/287 |
| 5,455,417 A | 10/1995 | Sacristan | 250/293 |
| 5,479,815 A | 1/1996 | White et al. | 73/23.3 |
| 5,492,867 A | 2/1996 | Kotvas et al. | 250/292 |
| 5,508,204 A | 4/1996 | Norman | 436/161 |
| 5,536,939 A | 7/1996 | Freidhoff et al. | 250/288 |
| 5,541,408 A | 7/1996 | Sittler | 250/286 |
| 5,644,131 A | 7/1997 | Hansen | 250/287 |
| 5,654,544 A | 8/1997 | Dresch | 250/287 |
| 5,723,861 A | 3/1998 | Carnahan et al. | 250/292 |
| 5,736,739 A | 4/1998 | Uber et al. | 250/293 |
| 5,763,876 A | 6/1998 | Pertinarides et al. | 250/288 |
| 5,789,745 A | 8/1998 | Martin et al. | 250/286 |
| 5,801,297 A | 9/1998 | Mifsud et al. | 73/23.34 |
| 5,801,379 A | 9/1998 | Kouznetsov | 250/288 |
| 5,811,059 A | 9/1998 | Genovese et al. | 250/292 |
| 5,834,771 A | 11/1998 | Yoon et al. | 250/293 |
| 5,838,003 A | 11/1998 | Bertsch et al. | 250/288 |
| 5,846,331 A * | 12/1998 | Miyamoto | 118/723 R |
| 5,852,302 A | 12/1998 | Hiraishi et al. | 250/286 |
| 5,869,344 A | 2/1999 | Linforth et al. | 250/287 |
| 5,965,882 A | 10/1999 | Megerle et al. | 250/288 |
| 5,998,788 A | 12/1999 | Breit | 250/288 |
| 6,035,101 A * | 3/2000 | Sajoto et al. | 392/416 |
| 6,049,052 A | 4/2000 | Chutjian et al. | 250/286 |
| 6,051,832 A | 4/2000 | Bradshaw | 250/286 |
| 6,055,151 A | 4/2000 | Tormey et al. | 250/286 |
| 6,066,848 A | 5/2000 | Kassel et al. | 250/288 |
| 6,107,628 A | 8/2000 | Smith et al. | 250/287 |
| 6,124,592 A | 9/2000 | Spangler | 250/292 |
| 6,157,029 A | 12/2000 | Chutjian et al. | 250/292 |
| 6,157,031 A | 12/2000 | Prestage | 250/288 |
| 6,180,414 B1 | 1/2001 | Katzman | 436/181 |
| 6,188,067 B1 | 2/2001 | Chutjian et al. | 250/293 |
| 6,200,539 B1 | 3/2001 | Sherman et al. | 250/286 |
| 6,262,416 B1 | 7/2001 | Chutjian et al. | 250/286 |
| 6,281,494 B1 | 8/2001 | Chutjian et al. | 250/287 |
| 6,309,532 B1 * | 10/2001 | Tran et al. | 205/687 |
| 6,323,482 B1 | 11/2001 | Clemmer et al. | 250/287 |
| 6,407,382 B1 * | 6/2002 | Spangler | 250/286 |
| 6,479,815 B1 | 11/2002 | Goebel et al. | 250/287 |
| 6,495,823 B1 | 12/2002 | Miller et al. | 250/286 |
| 6,504,149 B2 | 1/2003 | Guevremont et al. | 250/287 |
| 6,509,562 B1 | 1/2003 | Yang et al. | 250/282 |
| 6,512,224 B1 | 1/2003 | Miller et al. | 250/288 |
| 6,540,691 B1 | 4/2003 | Philips | 600/532 |
| 6,618,712 B1 | 9/2003 | Parker et al. | 250/288 |
| 6,639,212 B1 * | 10/2003 | Guevremont et al. | 250/282 |
| 6,653,627 B2 | 11/2003 | Guevremont | 250/282 |
| 6,680,203 B2 | 1/2004 | Dasseaux et al. | 436/86 |
| 6,690,004 B2 | 2/2004 | Miller et al. | 250/281 |
| 6,703,609 B2 | 3/2004 | Guevremont | 250/282 |
| 6,713,758 B2 | 3/2004 | Guevremont | 250/286 |
| 6,753,522 B2 | 6/2004 | Guevremont | 250/281 |
| 6,770,875 B1 | 8/2004 | Guevremont | 250/281 |
| 6,774,360 B2 | 8/2004 | Guevremont | 250/282 |
| 6,787,765 B2 | 9/2004 | Guevremont | 250/282 |
| 6,799,355 B2 | 10/2004 | Guevremont | 250/281 |
| 6,806,466 B2 | 10/2004 | Guevremont | 250/286 |
| 6,815,668 B2 * | 11/2004 | Miller et al. | 250/286 |
| 2001/0030285 A1 | 10/2001 | Miller et al. | 250/288 |
| 2002/0070338 A1 | 6/2002 | Loboda | 250/287 |
| 2002/0134932 A1 | 9/2002 | Guevremont et al. | 250/286 |
| 2003/0020012 A1 | 1/2003 | Guevremont | 250/287 |
| 2003/0038235 A1 | 2/2003 | Guevremont et al. | 250/286 |
| 2003/0052263 A1 | 3/2003 | Kaufman et al. | 250/282 |
| 2003/0089847 A1 | 5/2003 | Guevremont et al. | 250/286 |
| 2003/0132380 A1 | 7/2003 | Miller et al. | 250/286 |
| 2004/0094704 A1 | 5/2004 | Miller et al. | 250/287 |

FOREIGN PATENT DOCUMENTS

| | | |
|---|---|---|
| SU | 1337934 A2 | 9/1987 |
| SU | 1627984 A2 | 2/1991 |
| SU | 1405489 A1 | 6/1998 |
| SU | 1412447 A1 | 6/1998 |
| SU | 1485808 A1 | 6/1998 |
| WO | WO96/19822 | 6/1996 |
| WO | WO97/38302 | 10/1997 |
| WO | WO99/21212 | 4/1999 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO-01/69217 A2 | 9/2001 |
| WO | WO 01/69220 A2 | 9/2001 |
| WO | WO 01/69647 A2 | 9/2001 |
| WO | WO 02/71053 A2 | 9/2002 |

OTHER PUBLICATIONS

E. V. Krylov, "A Method of Reducing Diffusion Losses in A Drift Spectrometer," *Technical Physics*, 4d(1):113-116 (1999).

"Advanced Cross-Enterprise Technology Development for NASA Missions," Revised NASA Research Announcement NRA99-OSS-05 pp. 1-C19 (1999).

Buryakov, et al., "Drift Spectrometer for the Control of Amine Traces in the Atmosphere," *J. Anal. Chem.* 48(1):112-121 (1993).

Handy, et al., "Determination of Nanomolar Levels of Perchlorate in Water by ESI-FAIMS-MS," *J. Anal. At. Spectrometry* 15:907-911 (2000).

Buryakov, et al., "Separation of Ions According to Mobility in A Strong AC Electric Field," *Letters to Journal of Technical Physics*, 17:11-12 (1991).

Guevremont, Roger and Purves, Randy W., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom. 10:492-501 (1999).

Verenchikov, A.N. et al., Analysis ions in solutes be gaseous ion analyzer. "Chemical Analysis of the Environmental Objects," red. Malakhov. Novosibirsk, Nauka, pp. 127-134(1991).

Riegner D.E., et al., "Qualitative Evaluation of Field Ion Spectrometry for Chemical Warfare Agent Detection," Proceedings of the ASMS Conference on Mass Spectrometry and Allied Topics, pp. 473A-473B, (Jun. 1997).

Carnahan, B., et al., "Field Ion Spectrometry—A New Analytical Technology for Trace Gas Analysis," *ISA*, 51(1):87-96, (1996).

Carnahan, B., et al., "Field Ion Spectrometry—A New Technology for Cocaine and Heroin Detection," *SPIE*, 2937:106-119, (1997).

Buryakov, I.A., et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes, 128:143-148, (1993).

Miller, R.A., et al., "A Novel Micromachined High-Field Asymmetric Waveform-Ion Mobility Spectrometer," *Sensors and Actuators B*, B67(3):300-306, (2000).

Barnett, D.A., et al., "Isotope Separation Using High-Field Asymmetric Waveform Ion Mobility Spectrometry," *Nuclear Instruments & Methods in Physics Research*, 450(1):179-185, (2000).

Guevremont, R., et al., "Calculation of Ion Mobilities From Electrospray Ionization High-Field Asymmetric Waveform Ion Mobility Spectrometry Mass Spectrometry," *Journal of Chemical Physics*, 114(23):10270-10277, (2001).

Pilzecker, P., et al., "On-Site Investigations of Fas Insulated Substations Using Ion Mobility Spectrometry for Remote Sensing of $SF_6$ Decomposition," *IEEE*, pp. 400-403, (2000).

Krylov, E.V., "Pulses of Special Shapes Formed on a Capacitive Load," *Instruments and Experimental Techniques*, 40(5):628, (1197). Also cited in Database Nauka/Interperiodika 'Online!, International Academic Publishing Company (IAPC), Russia; E. Krylov.

Burykov, I.A., et al., *Device and Method For Gas Electrophoresis, Chemical Analysis of Environment*, edit. Prof. V. V. Malakhov, Novosibirsk: Nauka, (1991) pp. 113-127.

Raizer, Y. P., et al., *Radio-Frequency Capacitive Discharges*, CRC Press, pp. 1-3, (1995).

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Javahery, G., et al., A Segmented Radiofrequency-Only Quadrupole Collision Cell for Measurements of Ion Collision Cross Section on a Triple Quadrupole Mass Spectrometer, J. Am. Soc. Mass. Spectrom. 8:697-702 (1997).

Basile, F., "A Gas Sample Pre-concentration Device Based on Solid Phase Microextraction (SPME) and Temperature Programmed Desorption (TPD)," Instrumentation Sci. Tech., (2003), pp. 155-164, 31(2).

Demirev, P.A., et al., Microorganism Identification by Mass Spectrometry and Protein Database Searches, (1999), pp. 2732-2738, 74(14).

Demirev, P.A., et al., "Tandem Mass Spectrometry of Intact Proteins for Characterization of Biomarkers from *Bacillus cereus* T spores," Analytical Chem., (2001), pp. 5725-5731, 73(23).

Eiceman, G.A., et al., "Miniature radio-frequency mobility analyzer as a gas chromatographic detector for oxygen-containing volatile organic compounds, pheromones, and other insect attractants," J. Chomatography, (2001), pp. 205-217, 917.

Elhany, E., et al., "Detection of Specific anthracis Spore Biomarkers by Matrix-Assisted Laser Desorption / Ionization Time-Of-Flight Mass Spectrometry," Rapid Commun. Mass. Spectrom., (2001), pp. 2110-2116, 15(22).

Fox, A., et al., "Determination of Carbohydrate Profiles of *Bacillus anthracis* and *Bacillus cereus* Including Identification of O-Methyl Methylpentoses Using Gas Chromatography-Mass Spectrometry," J. Clin. Microbiol. (1993) pp. 887-894, 31(4).

Hathout, Y., et al., "Identification of Bacillus Spores by Matrix-Assisted Laser Desorption Ionization Mass Spectrometry," Appl. Environ Microbiol. (1999), pp. 4313-4319, 65(10).

Krishnamurthy, T., et al., "Liquid Chromatography/Microspray Mass Spectrometry for Bacterial Investigations," (1999), pp. 39-49, 13.

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio-frequency ion mobility spectrometer for chemical vapor detection," Sensors and Actuators, (2001), pp. 301-312, A91.

Mowry, C., et al., "Rapid Detection of Bacteria with Miniaturized Pyrolysis-Gas Chromatographic Analysis," Proc. Of SPIE, (2001), pp. 83-90, 475.

Phillips, M., "Breath tests in medicine," Scientific American, (1992), pp. 74-79, 267 (1).

Phillips, M., "Method for the Collection and Assay of Volatile Organic Compounds in Breath," Analytical Biochemistry, (1997), pp. 272-278, 247.

Shute, L.A. et al., "Curie-point Pyrolysis Mass Spectrometry Applied to Characterization and Identification of Selected Bacillius Species," J. General Micro., (JGMIAN) (1984), pp. 343-355, 130(2).

Vaidyanathan, S., et al., "Flow-Injection Electrospray Ionization Mass Spectrometry of Crude Cell Extracts for High-Throughput Bacterial Indentification," J. Am. Soc. Mass. Spectrom., (2002) pp. 118-128, 13.

Wang, Z., et al., "Mass Spectrometric Methods for Generation of Protein Mass Database Used for Bacterial Identification," Analytical Chem., (2002), pp. 3174-3182, 74(13).

Schneider, A. et al., High Sensitivity GC-FIS for Simultaneous Detection of Chemical Warefare Agent, Mine Safety Appliances Co., Pittsburgh, PA, USA, (2000), AT-Process, pp. 124-136, 5(3,4), CODEN:APJCFR ISSN: 1077-419X.

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

* cited by examiner

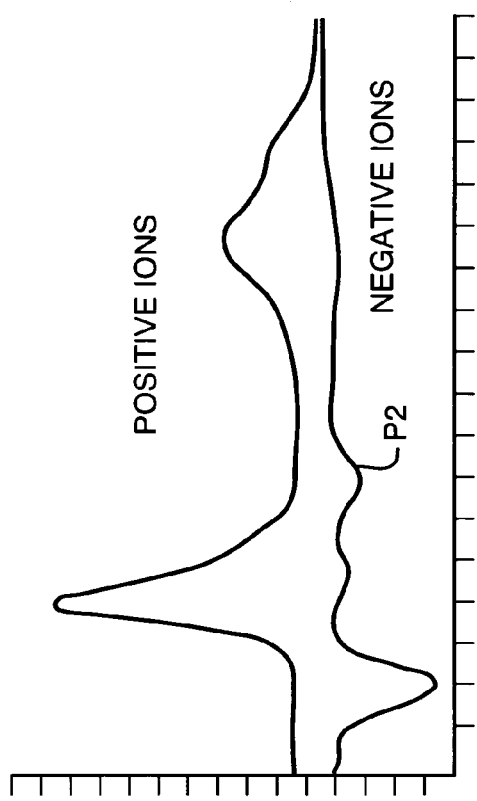
FIG. 1E(2)
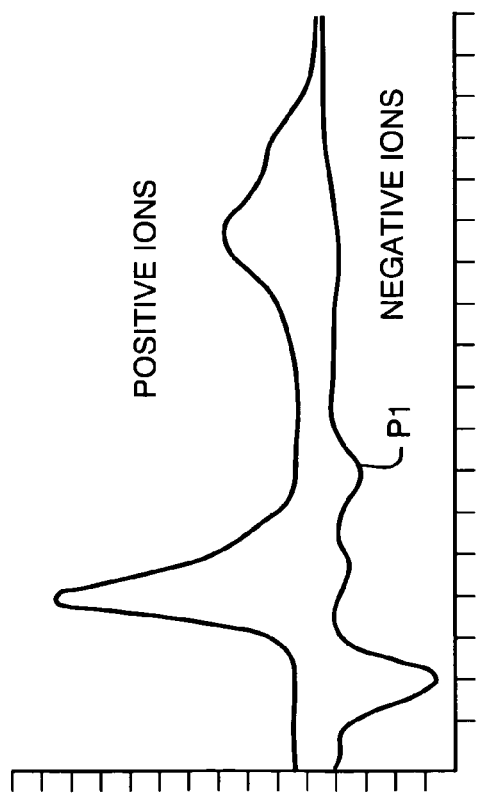
FIG. 1E(1)

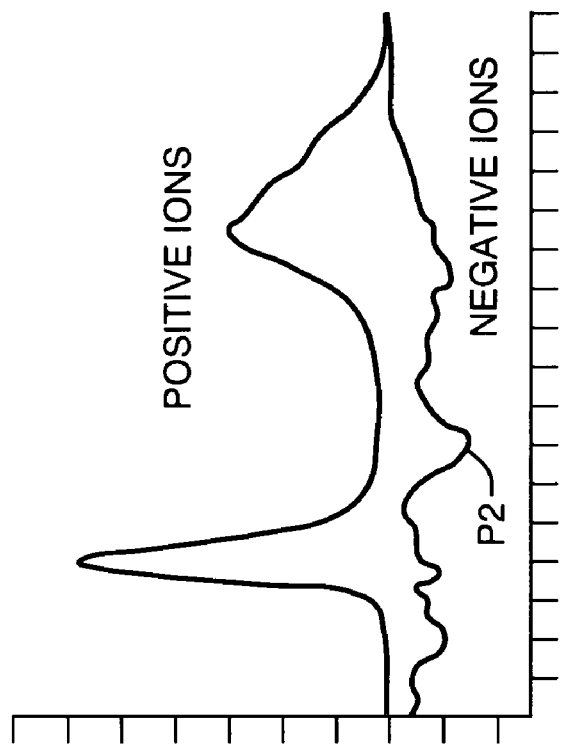
FIG. 1F(2)
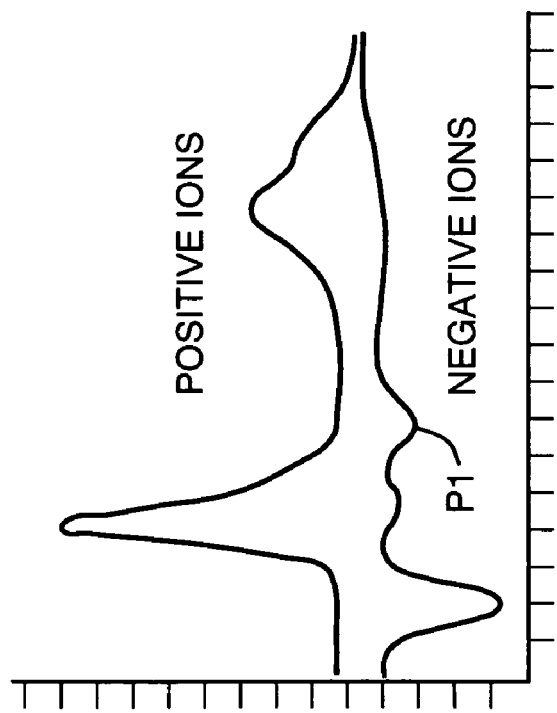
FIG. 1F(1)

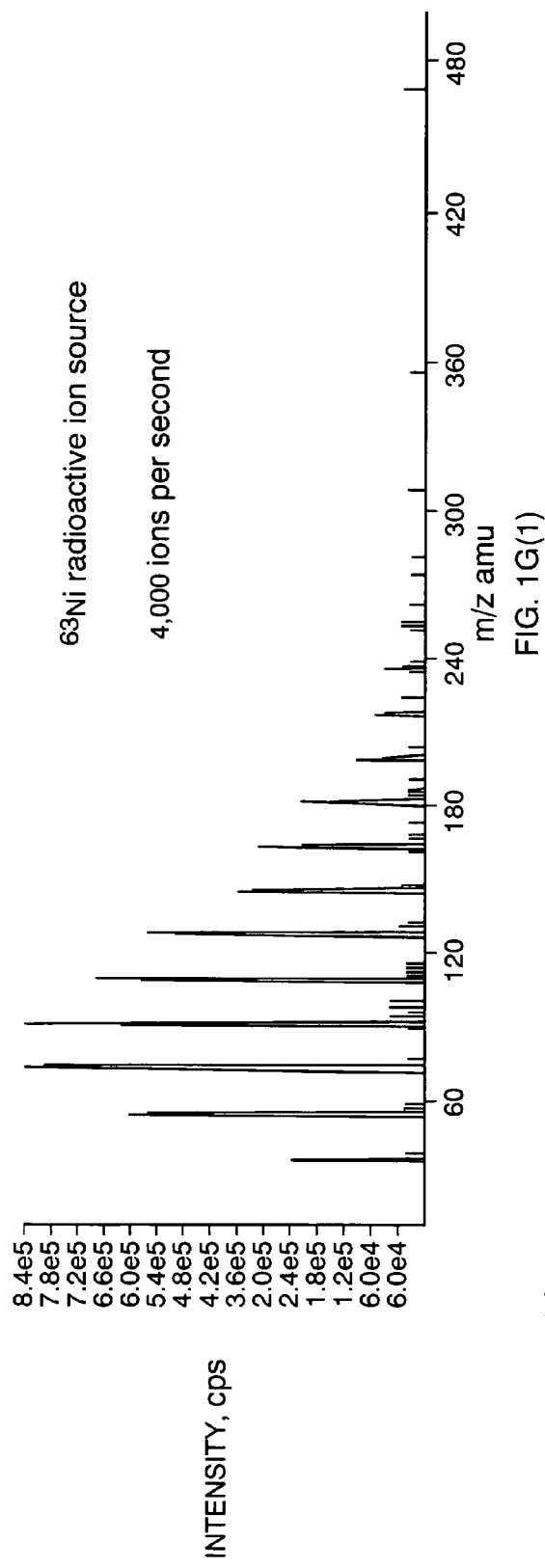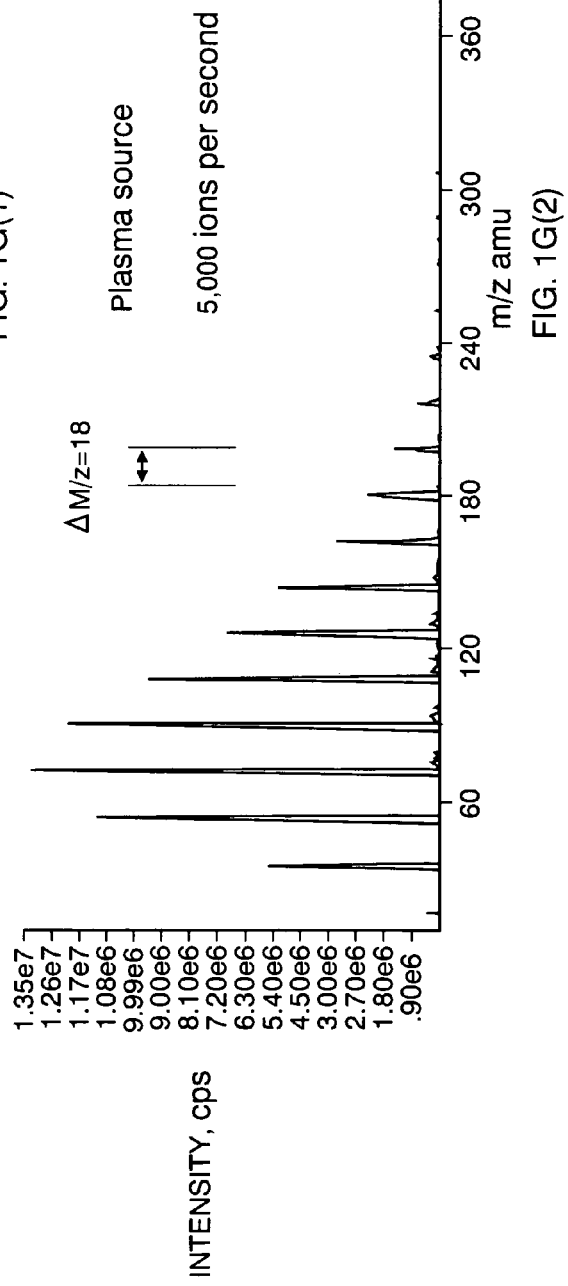
FIG. 1G(1)
FIG. 1G(2)

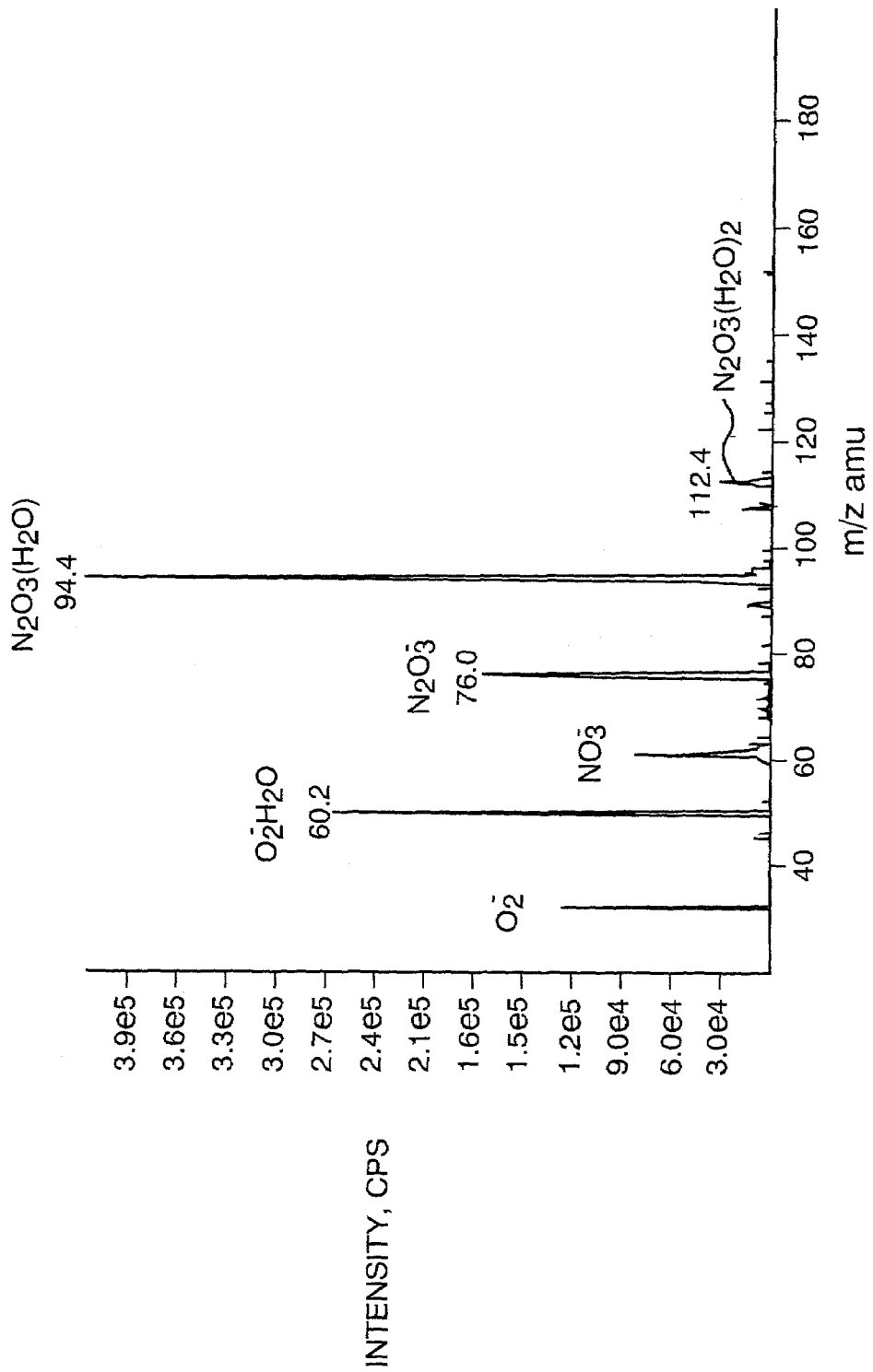
FIG. 1H(1)

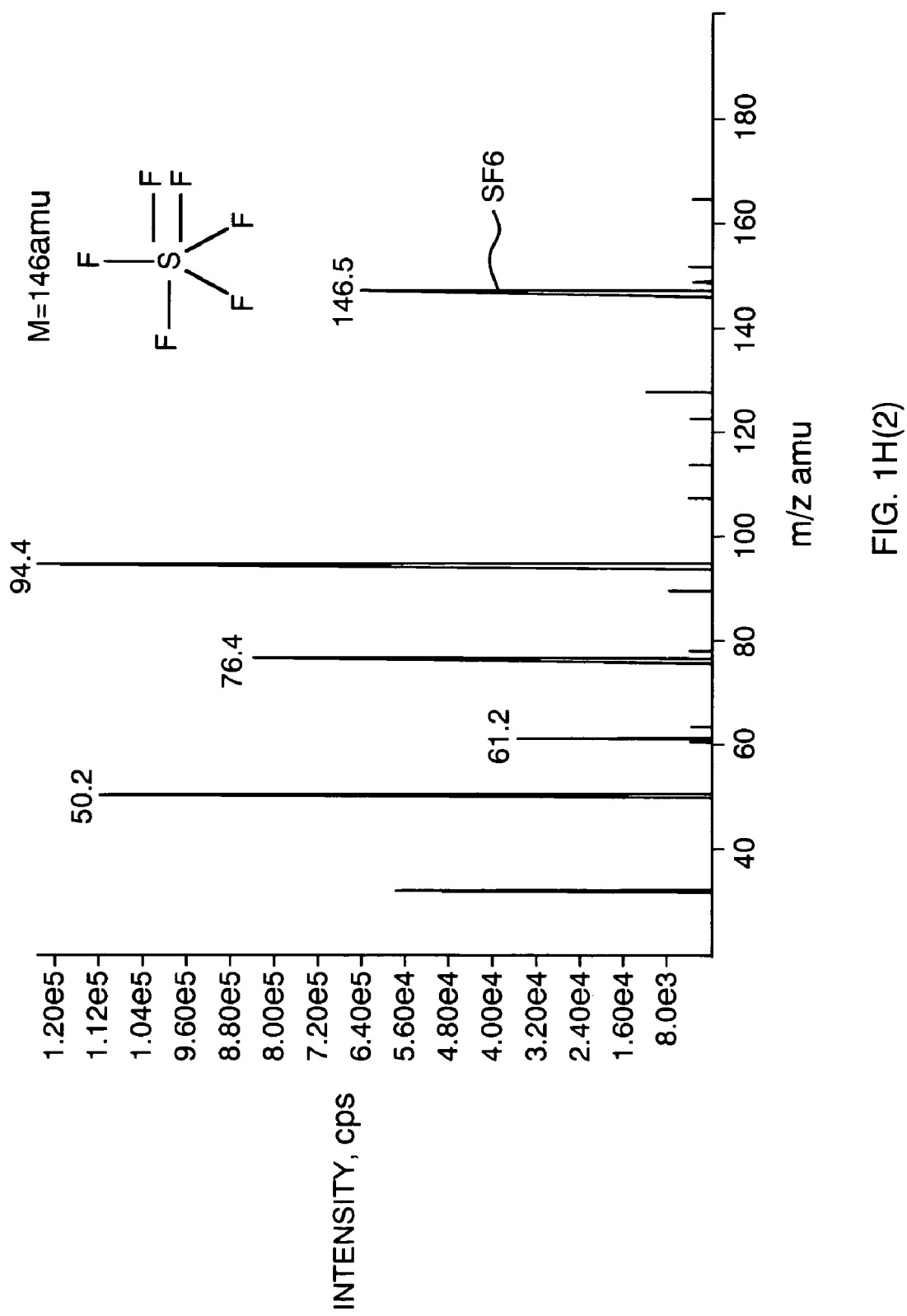
FIG. 1H(2)

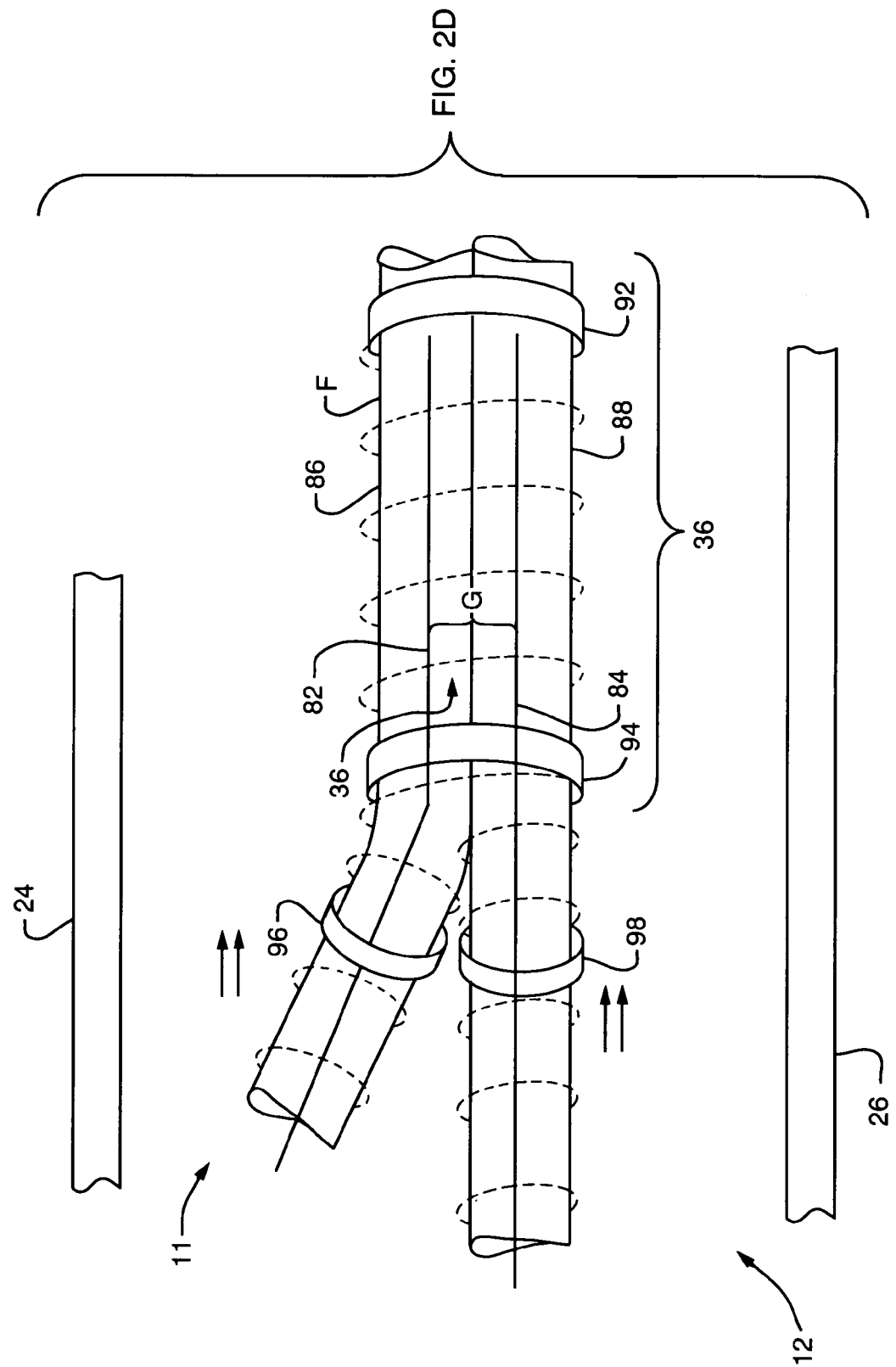

CAPACITIVE DISCHARGE PLASMA ION SOURCE

CROSS REFERENCE TO RELATED APPLICATIONS

This application claims the benefit of a prior U.S. Provisional Application Ser. No. 60/310,902 filed Aug. 8, 2001 entitled, "Miniature Atmospheric Pressure Capacitive Discharge Ionization Source", Ser. No. 60/335,219 filed Oct. 25, 2001 entitled "Radio Frequency Capacitive Discharge Ionizer for Analyzer", Ser. No. 60/340,815 filed Dec. 12, 2001 entitled "Radio Frequency Capacitive Discharge Ionizer for Analyzer", and Ser. No. 60/388,052 filed Jun. 12, 2002 entitled "Plasma Ionization Source for Metal Ion and Other Analysis", the entire contents of all of such applications being hereby incorporated by reference.

BACKGROUND OF THE INVENTION

The present invention relates to an ionization source, and more particularly, to a gas-discharge ionizer.

Creation of ionized particles is a useful tool for many applications, such as for ignition of lasing or to assist chemical analysis, among other uses. In some equipment, high energy radioactive sources of alpha or beta particles are employed for the ionization process. However, because of their potential health hazard, wide-spread use of equipment using radioactive ionization sources in many applications has been limited.

Equipment such as gas analyzers, among other equipment, that uses radioactive sources are therefore limited in their utility. While some smoke alarms use radioactive sources, the amount of ionization is low, and still requires government regulation.

Photo-ionization and UV ionization techniques are employed as alternatives to use of a radioactive ionization source. These ionization approaches have relatively low ionization energies, typically 8-11 eV, which limits the types of molecules that can be ionized. Also these devices are typically delicate and fragile, and hence are generally not suitable to operate in harsh environments or in applications requiring a significant amount of manual handling. Furthermore, UV devices require some maintenance and the intensity degrades overtime. As such, even though photo-ionization and UV ionization devices are typically safer to operate than radioactive ionization sources, they are not a viable or cost-effective option in many circumstances, whether for general equipment use or for gas analyzers.

Corona discharge is another source of non-radioactive ionization. It provides high energy in a compact package. However, this process is not stable and often-times contaminates the sample, as would interfere with analytical results. Furthermore, the generated ion species depends upon the applied voltage.

RF discharge ionization reduces some of these disadvantageous effects. RF discharges are subdivided into inductive and capacitive discharges, differing in the way the discharge is produced.

Inductive methods are based on electromagnetic induction so that the created electric field is a vortex field with closed lines of force. Inductive methods are used for high-power discharges, such as for production of refractory materials, abrasive powders, and the like. In PCT publication number WO 01/69220, an inductively coupled plasma ionization technique is disclosed. Ions produced within the plasma source are provided to a high Field Asymmetric Waveform Ion Mobility Spectrometry (FAIMS) analyzer within a low pressure chamber of a mass spectrometer and in fluid communication with the plasma source for receiving ions therefore. The ions are separated in the FAIMS and at least some of the ions are provided to the mass spectrometer after separation. Inductively coupled ionization sources, such as described in WO 01/69220, tend to be power consuming, and further, the inductively coupled ionization sources are relatively complex, large and expensive.

Capacitive discharge methods are used to maintain RF discharges at moderate pressures p~1-100 Torr and at low pressures $p\sim10^{-3}$-1 Torr. The plasma in them is weakly ionized and non-equilibrium, like that of a corona discharge. Moderate-pressure discharges have found application in laser technology to excite $CO_2$ lasers, while low-pressure discharges are used for ion treatment of materials and in other plasma technologies. Varieties of radio-frequency capacitive discharge are discussed in Raizer, Shneider and Yatsenko, entitled Radio-Frequency Capacitive Discharges, © 1995 CRC Press LLC, with general background at pages 1-3.

In PCT publication number WO 96/19822, an RF ion source providing capacitively coupled ionization is described. The RF ion source is suitable for low power operation over a range of pressures in air. The source includes anode and cathode electrodes connected to an RF signal supply. The anode is adapted to provide a surface area over which a plasma discharge may occur. In this way, the anode presents no more useful surface than is required to accommodate the optimum area of the plasma discharge, preventing plasma wander and enhancing the stability of the discharge over known ion sources. The ion source provides an effective discharge with very low power even at atmospheric pressure.

Capacitively coupled ionization sources, such as described in WO 96/19822, are more efficient than inductively coupled ionization sources but may contaminate the sample due to electrode surface contact with the gas sample and plasma, leading to secondary ion emissions. The gas sample may corrode the electrode surface, and electrons freed from the plasma molecules, produced by the gas sample interaction with the electric field between the electrodes, can strike the electrode plates and are removed from the plasma, thus causing the plasma to have a net positive charge and an average potential relative to the plates. This drives the ions with a high velocity into the electrodes and can lead to the release of electrode plate molecules from the electrode surface. Also, the chemicals in the gas sample or plasma can chemically react with or corrode the electrodes, which can contaminate the sample. This can cause chemical analysis errors.

In view of the foregoing, there is a felt need for a clean and stable ionization source that is compact, light-weight and inexpensive and delivers a relatively high level of ionization energy for analytical applications in gas (e.g., air) at pressures including atmospheric pressure.

It is therefore an object of the present invention to provide a clean and stable, non-radioactive, ionization source.

It is another object of the present invention to provide a clean and stable, non-radioactive, robust, ionization source that is suitable for analytical applications and the like.

It is a still another object of the present invention to provide a clean and stable, non-radioactive, robust, ionization source that is compact, light-weight and inexpensive and delivers a relatively high level of ionization energy for analytical applications and the like in gas (e.g., air) at pressures including atmospheric pressure.

It is a further object of the present invention to provide a clean and stable, non-radioactive, robust, ionization source that provides positive and negative ions simultaneously.

SUMMARY OF THE INVENTION

The present invention meets the need for non-radioactive ionization sources. More specifically, we have discovered an RF-driven capacitive discharge method and apparatus for generation of a high energy, clean and stable plasma for sample ionization. A preferred embodiment of the invention is useful as an ionization source for chemical analysis and other applications and is operable in gas (e.g., air) at pressures including atmospheric pressure.

One embodiment of the invention provides a capacitive discharge apparatus that generates a clean and stable plasma in gas (e.g., air) at pressures including at or around atmospheric pressure. The apparatus includes two electrodes spaced by a gap. A plasma is formed in the gap.

In various embodiments of the invention, either one or both of the electrodes is isolated from the plasma environment. More particularly, to reduce or prevent electrode surface molecular discharge and to limit or prohibit ion contamination, a low or non-conductive material, whether an insulator or dielectric, is used to isolate the electrodes. This protects the electrodes from corrosion and electron impact.

Therefore a plasma generator apparatus of the invention is able to ionize a wide range of compounds without contamination from electrode surface molecular discharge and ion contamination. A preferred embodiment of the invention provides a clean and stabilized plasma generator with both electrodes being insulated from the plasma environment. However, good results may also be obtained in practice of the invention when one only of the electrodes is insulated.

In addition to the foregoing, a high power RF electric field is applied to the electrodes to generate the plasma in the gap by use of a resonant circuit. The RF-driven and isolated electrodes produce a stable plasma and have a long service life, producing little or no contaminants in the plasma.

In operation, when a carrier gas and a chemical sample are introduced into the plasma, the gas, such as air, and the sample, are ionized and are passed downstream for further processing. It is a further benefit that the invention can produce plasma having both positive and negative ions.

The present invention allows control of energy imparted to the plasma. In one case, we can generate a plasma, preferably by "soft" atmospheric pressure ionization (API); in another case we can increase of the energy into the plasma and perform hard ionization. It will be appreciated that ionization may be characterized as "soft" or "hard" depending on the electric field energy pumped into the gas discharge. Soft ionization involves charge attraction and transfer reactions and produces molecular ions, and is non-destructive. Hard ionization results from electron impact and produces fragment ions. Both types of ionization may be useful in practice of the invention. For example, soft ionization may be selected for analysis of in-tact ionized molecules, while fragmentation may generate additional useful data when complex mixtures are analyzed.

In a preferred embodiment, we use a high efficiency drive circuit to stabilize the plasma. In one embodiment we use a resonant drive circuit to produce a high frequency (RF) high voltage for increased discharge stability and decreased power consumption. In a preferred embodiment, we use a resonant circuit with system stability provided via negative feedback. In another embodiment, additional operating efficiency is achieved by using a pulsed high frequency high voltage drive.

Various electrode configurations are within the spirit and scope of the invention, including planar, cylindrical, curved, molded, wire, and needle shapes which present any variety of flat or curvilinear ionization surfaces. The electrodes may be parallel or at an angle to each other. In one embodiment, the gas sample flows between the electrodes, and in another embodiment, the gas sample flows around the electrodes.

Among other advantages, the capacitively coupled ionization device of the present invention is clean and stable, robust, light-weight, compact, and can operate at, above and below atmospheric pressure. It is highly efficient and cost-effective and provides high ionization intensities that are practical for a wide range of applications, such as, but not limited to, gas analysis, while consuming low power. The isolated electrodes produce a stable plasma and have a long service life, producing little or no contaminants in the gas sample.

Since the device is operable in a common RF frequency range and is a non-radioactive source, it does not have to be federally regulated as in the manner of radioactive sources, and hence can be conveniently used in a wide range of applications. Thus embodiments of the present invention therefore meet the need for non-radioactive ionization sources and overcomes the inadequacy of known inductive and capacitive ionization sources to provide clean and stable ionization sources for generation of charged particles, such as is useful for gas analysis and other applications.

The present invention includes the innovations of commonly assigned and owned provisional applications referred to as Attorney Docket M008, entitled Miniature Atmospheric Pressure Capacitive Discharge Ionization Source, By Raanan A. Miller and Evgeny Krylov, U.S. Provisional Application No. 60/310,902, filed Aug. 8, 2001; Attorney Docket M018, entitled Radio Frequency Capacitive Discharge Ionizer For Analyzer, by Raanan A. Miller and Erkinjon G. Nazarov, U.S. Provisional Application Ser. No. 60/335,219, filed Oct. 25, 2001; and Attorney Docket M031R, entitled Radio Frequency Capacitive Discharge Ionizer For Analyzer, by Raanan A. Miller, Erkinjon G. Nazarov, and Evgeny Krylov, U.S. Provisional Application Ser. No. 60/340815, filed Dec. 12, 2001, all incorporated herein by reference.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 2B-2D are alternative embodiments of the capacitive discharge structure of the invention.

FIG. 5-6 Omit.

DETAILED DESCRIPTION OF THE INVENTION

Figure 1A:
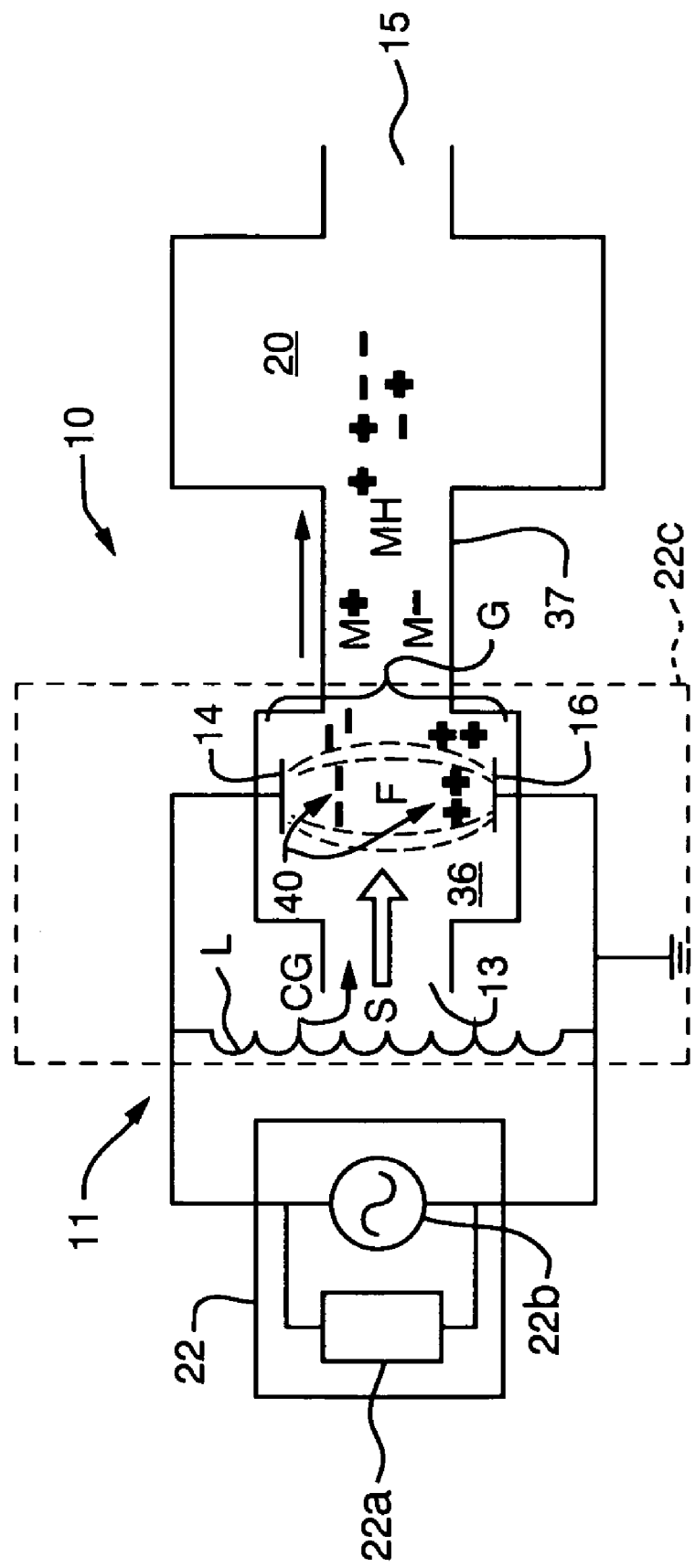
FIG. 1A is a generalized block diagram of apparatus employing a capacitive discharge plasma ionizer in practice of the invention.

FIG. 1A is a generalized block diagram of a system 10 in practice of the invention used to analyze the composition of chemical compounds in a gas sample S. The system 10 includes a capacitive discharge plasma ionization source 11 and a detector 20. The detector may be a mass spectrometer (MS), ion mobility spectrometer (IMS), high-field asymmetric waveform ion mobility spectrometer (FAIMS), time-of flight spectrometer (TOF), or the like. In this embodiment, the capacitive discharge plasma ionization source 11 is separate from but in communication with spectrometer 20. Alternatively, the source 11 may be integrated into the spectrometer to form an integrated system 10.

Capacitive discharge plasma ionization source 11 includes a pair of electrodes 14, 16, which are preferably isolated, or insulated, as further described below. When a sufficient voltage is supplied across electrodes 14, 16, a discharge field F is established. Now the gas is flowed into the field in the gap G between the electrodes; the gas is thus ionized by capacitive discharge between the electrodes. This discharge ionization produces a plasma 40 from the air, with both positive and negative ions, such as shown in FIG. 1G(2) and FIG. 1H(1), usually including $(H2O)_n$, $H^+$, $O^-$, $O_2^-$, $O_3^-$, $(N_xO_n)^+$, and $(N_xO_y)^-(H_2O)_n$.

In operation, a gas and sample S feeds through inlet 13 into ionization region 36. The gas again is ionized by the discharge in the RF field F between the electrodes forming the plasma ions. The plasma in turn ionizes the sample S and forms ions $M^+$, $MH^+$, and $M^-$. All of the generated ions now present in the ionization region 36 exit through an outlet passage 37 for further utilization. In an analytical embodiment of the invention, these ions now proceed from passage 37 into spectrometer 20 for analysis.

Figure 1B:
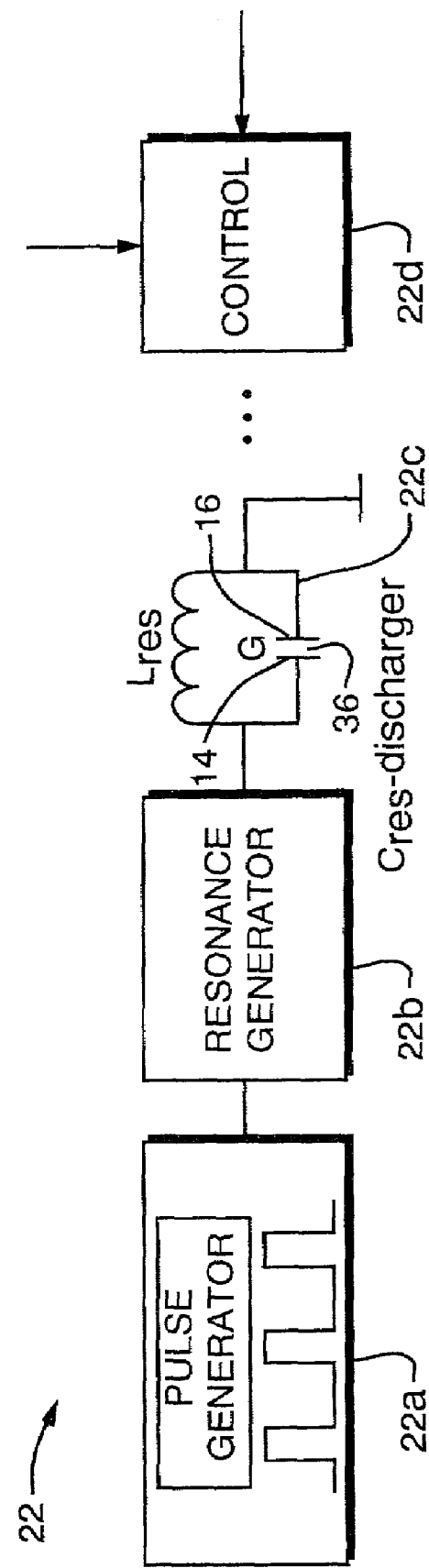
FIG. 1B is an illustrative resonant RF drive circuit of the capacitive discharge plasma ionizer in practice of the invention.

A preferred control and drive circuit 22 of the invention is shown in FIG. 1A and in more detail in FIG. 1B, including a pulse generator 22a, a resonance generator 22b, and a resonant circuit 22c. The resonant circuit 22c includes electrodes 14, 16 spaced by gap G) and inductor L. As will be appreciated by a person skilled in the art, a microchip or other logic or controller device 22d may also be supplied in communication with the drive circuit 22, and also possibly having inputs from other system feedback or data sources, to affect total system control.

We have found that use of the resonant drive 22 to produce a high frequency (RF) high voltage increases discharge stability and decreases power consumption. In a preferred embodiment, the resonant drive circuit 22 also provides system stability via negative feedback. More particularly, it will be appreciated that plasma pumping energy strongly depends on field strength. If applied voltage (and electric field correspondingly) rises, then discharge energy increases. This results in increasing rate of ionization and consequently increase in discharge conductivity. Unchecked, this increase could result in a excessive increase in plasma energy and heating.

However, if we form the electrodes 14, 16 as a capacitor in L-C resonant circuit 22c, then stability can be obtained. If the capacitor's conductivity increases, then the Q-factor of the resonant circuit decreases. Since applied voltage is proportional to the Q-factor, the voltage decreases as well. Thus electrodes 14, 16 are part of a negative feedback loop to maintain the plasma at a desired energy level for a given drive voltage and frequency, preventing runaway plasma growth and overheating.

A particular drive circuit 22 design will depend on target plasma levels, electrode and gap dimensions, among other things, as will be appreciated by a person skilled in the art. Nevertheless, typically a high-frequency voltage, with an amplitude of several hundred volts, is required to initiate and maintain the discharge in atmospheric conditions. The reactive power in the megahertz frequency range will be tens of watts for a capacitive load of tens of picofarad. Therefore the present invention preferably employs a resonant oscillator with a capacitive load as a component of the output LC-circuit, as will be further appreciated by a person skilled in the art.

Figure 1C:
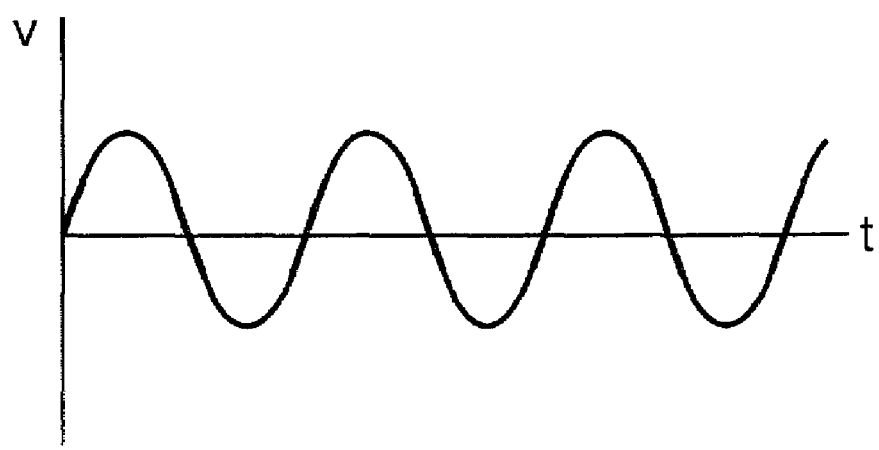
FIGS. 1C and 1D show alternative waveforms supplied by an RF drive circuit of the invention.
Figure 1D:
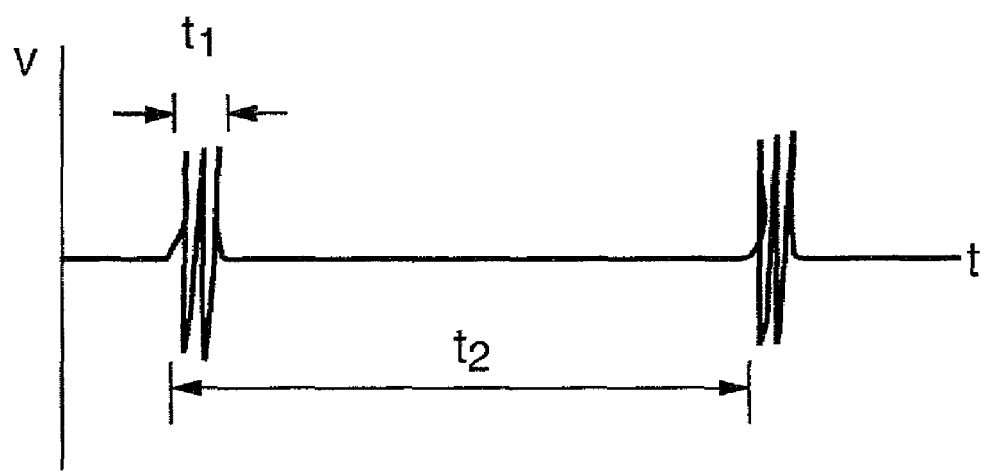
Figure 1L:
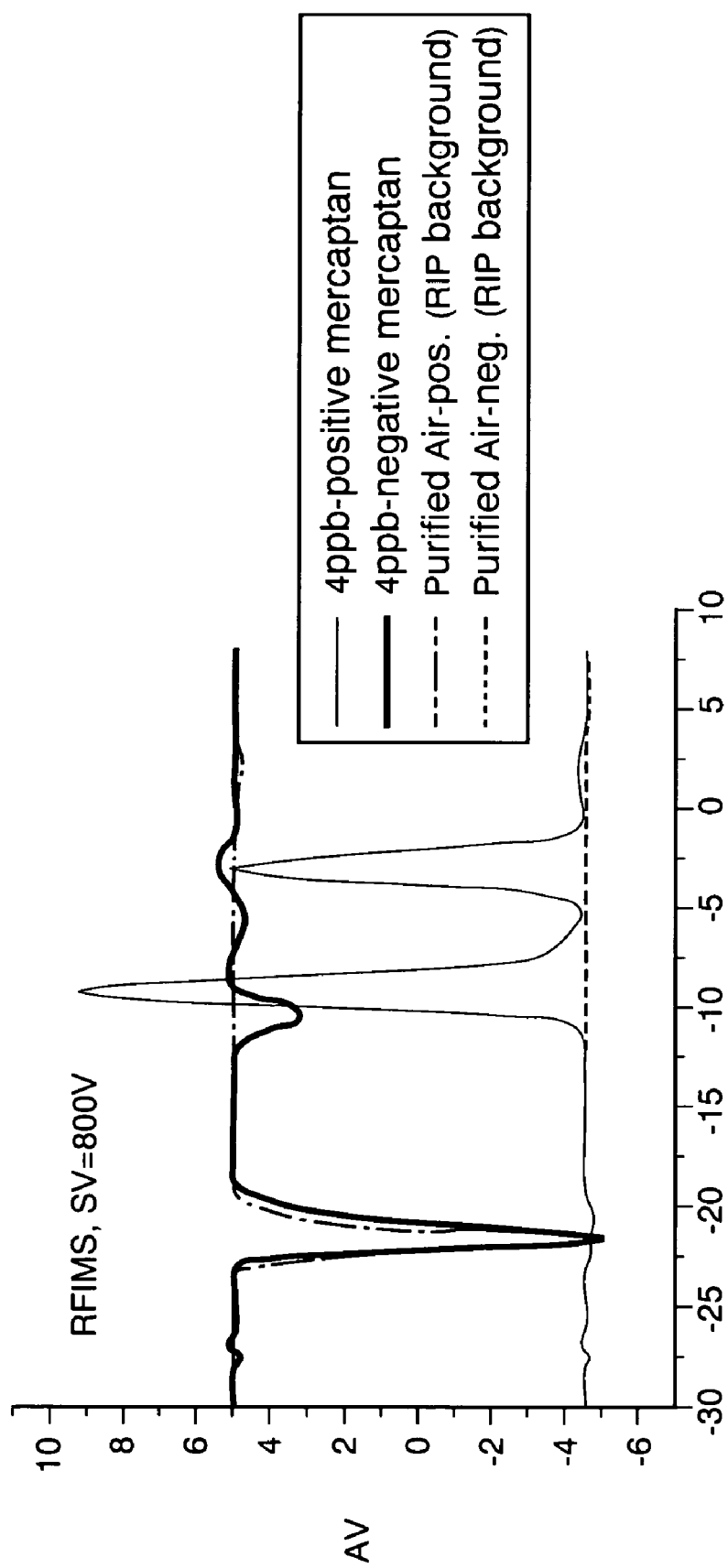
FIG. 1E shows an alternative embodiment of the invention where (1) positive and negative FAIMS spectra which can be generated by a capacitive discharge plasma ionization source of the invention with both electrodes insulated compared to (2) positive and negative spectra generated with a radioactive source.
FIG. 1F compares (1) the FAIMS spectra of FIG. 1E(2) for a radioactive source to (2) positive and negative spectra generated in practice a capacitive discharge plasma ionization source of the invention with only one electrode insulated.
FIG. 1G is a comparison of the mass positive spectra (1) from a radioactive source and (2) from an embodiment of the invention, detected by a mass spectrometer with a low plenum gas flow.
FIG. 1H shows negative mode mass spectrometer spectra for (1) pure air, and (2) pure air plus 20 ppm of $SF_6$(M=146), after plasma ionization in practice of the invention.
FIG. 1I shows FAIMS detection of mercaptan and purified air ionized in an embodiment of the capacitive gas discharge plasma ionizer of the invention.
FIG. 1J shows mass spectra for acetone generated and reproduced by ionization of acetone in practice of the invention.

In practice of the invention, the electric field has an RF component that may be of a standard or custom shape (e.g., sinusoidal, bias offset, pulse width modulated, or otherwise). For example, embodiments of the invention are operable with a sinusoidal high frequency high voltage waveform applied to electrodes 14, 16, as shown in FIG. 1C. Preferably further efficiency is achieved by using a pulsed ("packet") waveform, as shown in FIG. 1D.

Use of the packet waveform increases discharge stability, decreases power consumption, and further controls ionization efficiency. More specifically, the pulsed design follows from the recognition that a finite time interval is required for the plasma instability to reach the macrolevel. Therefore, energy is delivered to the discharge gap by short high frequency (RF) high voltage high intensity pulses, so that the instability does not have the time to develop. A dense plasma is formed in this case, since the ionization strongly depends on the energy. Once a pulse is switched off, dissipative processes suppress the development of the instability. If the pulse repetition period is comparable to the energy relaxation time in the plasma, its period-averaged parameters, including the degree of ionization, will be quasi stable. In one illustrative embodiment, the pulse had a frequency of about 1-20 MHz, a duration of about 1 msec, and a peak-to-peak voltage of about 1000-10000 volts. The duty cycle ($t_1/t_2$) of the packet waveform was approximately 1/11.

In any event, use of the packet waveform is beneficial. Because the efficiency of ionization of the plasma ionization device 11 is directly proportional to the voltage supply duty cycle, drive circuit 22 consumes less power (proportional to duty cycle) to provide the pulsed waveform versus the continuous waveform. Further, the service lifetime of the ionization device 11 increases by a factor of 5 to 10 time when the ionization device is powered with a pulsed packet waveform.

With either continuous or packet waveform, a sufficient RF voltage will be developed across electrodes 14, 16 to cause the local gas to electrically discharge and form a plasma. FIGS. 1E and 1F show positive and negative spectra produced in clean laboratory air at atmospheric pressure, detected using a FAIMS spectrometer.

FIG. 1E(1) shows positive and negative spectra which could be generated in an alternative embodiment of the invention by a capacitive discharge plasma ionization with both electrodes, 14, 16 being insulated, compared to (2) positive and negative spectra generated with a radioactive ionization source ($^{63}$Ni at 10 mCu). It is clearly shown in FIG. 1E that a non-radioactive ionization source of the invention (FIG. 1E(1)) could be substituted for a radioactive source (FIG. 1E(2)) to provide essentially the same performance.

In FIG. 1F, a comparison was made between the same radioactive source of FIG. 1F(1) against an embodiment of the invention with only one of electrodes 14, 16 being insulated. Nevertheless, the positive spectra are nearly identical between the $^{63}$Ni source of FIG. 1F(1) and the embodiment of the invention of FIG. 1F(2).

Discussion of the benefits of isolated electrodes will be discussed below, however we note here that the negative spectra in FIG. 1F(2) was somewhat degraded versus that of FIG. 1F(1). Yet the negative spectra still retain adequate information to be useful. For example, the species indicated by peak pi in the negative spectra of FIG. 1F(1) is clearly discerned as peak p2 in the negative spectra of FIG. 1F(2).

In addition to the foregoing, we have found that the plasma source of the invention is capable of providing adequate ionization energy in many applications, operating on as low as only a few watts (e.g., two watts in one embodiment). Furthermore, in comparison of FIGS. 1E and 1F, the beta source was capable of generating a maximum ion current of 4 p, while the invention delivered a maximum 12 pA. Therefore, it is evident that a clean, efficient and powerful plasma ionization source can be provided in practice of the invention.

We have clearly demonstrated the utility of the present invention as a viable substitute for a radioactive plasma source. More specifically, FIG. 1G is a comparison of the positive spectra (1) from a radioactive source and (2) from an embodiment of the invention, detected by a mass spectrometer with a low plenum gas flow (i.e., a barrier counter-flow of clean gas to prevent introduction of laboratory air into the MS). Frame (1) shows background mass spectra for $^{63}$Ni in an apparatus that generated 4,000 ions per second. Frame (2) is an embodiment of the invention that recreated the same or comparable spectra and yet with an ion production rate of 50,000 ions per second. It is therefore clear that the present invention is a rich source of ions for a broad range of applications. (It is further noted that while FIG. 1G shows MS results with a low plenum gas flow, the present invention is not limited to particular flow rates, whether in the plasma ionizer (sample and carrier gas) or in a FAIMS analyzer (ion flow) or at the front end of an MS (plenum).)

FIG. 1H shows negative mode mass spectrometer spectra for (1) pure air, and (2) pure air plus 20 ppm of $SF_6$, after plasma ionization in practice of the invention. Quite clearly, comparing the two frames, the $SF_6$ (M=146 amu) peak stands out and is clearly identified, while the background spectra retains its integrity.

Exceptional detection results may also be obtained using other detection devices. For example, in FIG. 1I a FAIMS (also known as RFIMS) spectrometer received an ionized output of a mercaptan sample and purified air as outputted by an embodiment of the capacitive gas discharge plasma generator of the invention. The negative and positive mercaptan (+/−mer.) peaks and background spectra are clearly defined.

Figure 1J:
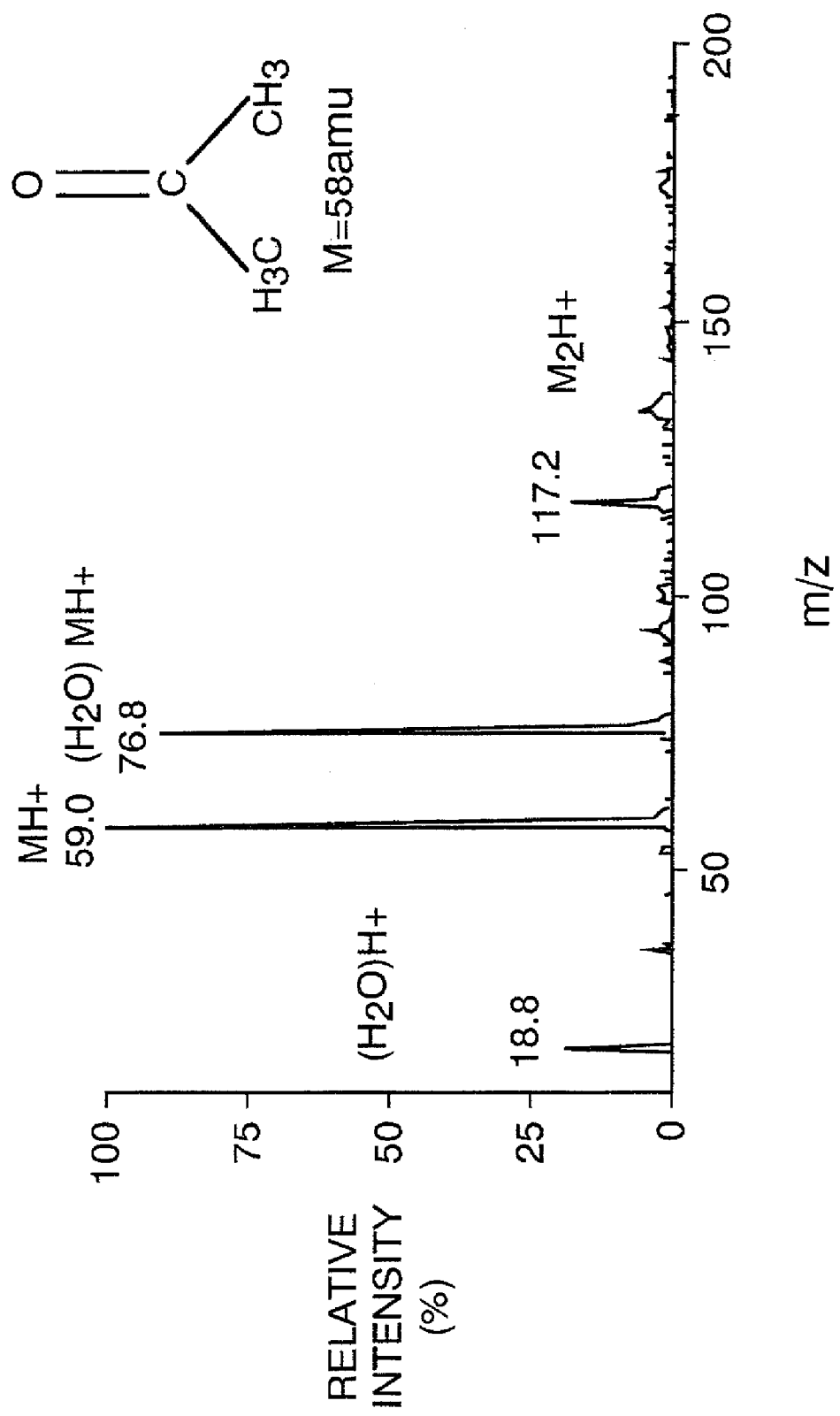

It is thus clear that the plasma generator of the invention is a useful and versatile non-radioactive plasma ionization source for a variety of applications. Further evidence of this utility, by way of additional illustration, is shown in FIG. 1J, where the mass spectra for acetone was generated and reproduced by ionization of acetone in practice of soft ionization within the invention. It will be understood that in practice of embodiments of the invention, this mass spectra can be used for the identification of acetone. Thus the simplicity and utility of the invention should now be appreciated as being quite broad.

Isolation of the electrodes 14, 16 from the plasma environment has beneficial effects. Therefore in embodiments of the invention, one or both electrodes are isolated. Preferably both electrodes are isolated, however, it is less common but possible where an embodiment of the invention could be used without any isolation of the electrodes. This might occur where stability is the primary motivation, for example.

Nevertheless, in a preferred embodiment of the invention, both electrodes 14, 16 are isolated, such as by use of insulating material. The insulator is used to separate the gas sample being ionized from the surfaces of the electrodes that are used to generate the plasma field F between the electrodes.

The insulator is preferably a dielectric material. A dielectric is a substance that is a poor conductor of electricity but an efficient supporter of an electrostatic field. Examples of dielectric materials include porcelain (ceramic), mica, glass, plastics, the oxides of various metals, and some liquids and gases, all of which may be employed as insulators on, around or in between electrodes 14, 16 in embodiments of the present invention.

A dielectric material serves two functions. First, its presence traps charges from the plasma, reducing the average potential of the plasma relative to the electrodes. This is important since the potential difference between the electrodes and the plasma defines how much ion bombardment of the electrode surface or dielectric takes place (and consequently decreases etching of the electrodes). The higher the potential difference, the more bombardment. This ion bombardment is unwanted since it leads to formation of ions from the electrode material in the sample plasma and contaminates the sample spectra. Second, the dielectric material tends to be inert so that reactive gases can be ionized without interaction with the electrodes. The resulting is a clean plasma ionization environment.

Furthermore, in one embodiment, a glass or crystal tube encloses the ionization region, including enclosing the resulting plasma (and disassociated electrons) within the electric field between the electrodes. Sample and carrier gas is flowed into this environment for ionization. In yet another embodiment, the electrodes are formed on the outside of an insulated structure that forms an insulated flow channel and the plasma is generated within the insulated channel between the insulated electrodes.

While these and other embodiments of the invention may now occur to a person skilled in the art, we disclose further embodiments of the invention by way of illustration and not by way of limitation. These and yet other variations are nevertheless within the spirit and scope of the present invention.

Figure 2A:
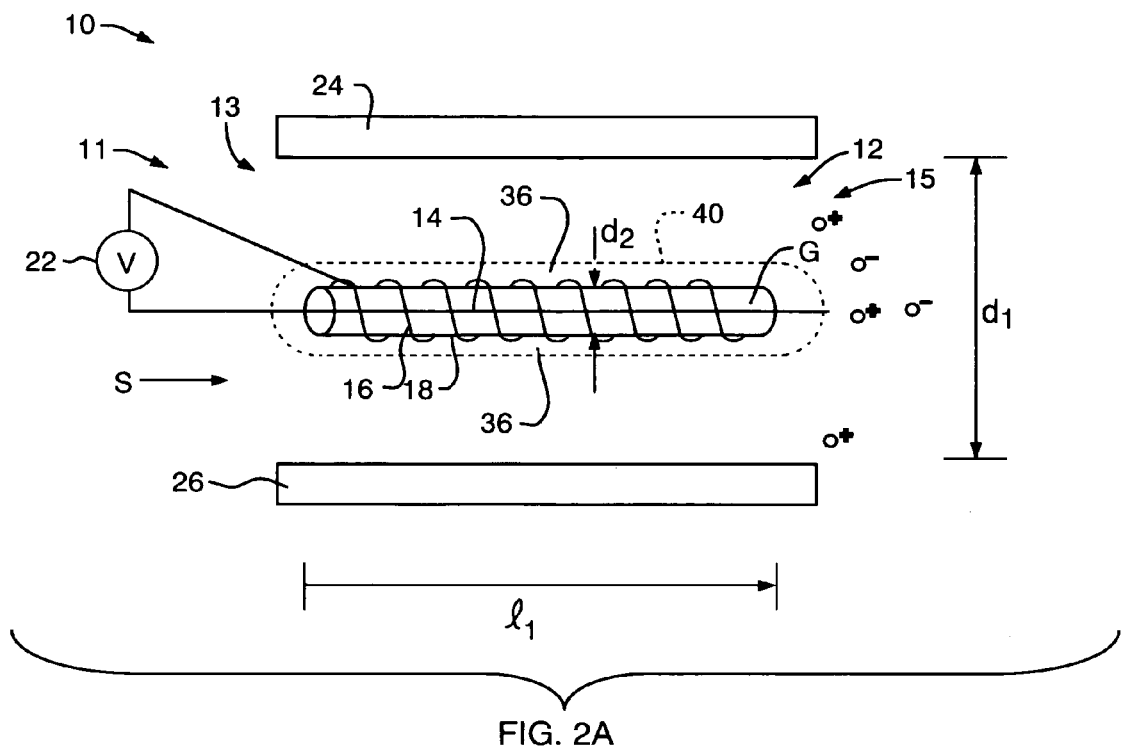
FIG. 2A shows an embodiment of a capacitive discharge plasma ionizer structure according to the present invention.

For example, referring to FIG. 2A, apparatus 10 includes a plasma ionization device 11 positioned within a flow channel 12. The ionization device 11 defines an ionization region 36 about the ionization device 11. Channel 12 has a planar geometry formed by an upper and a lower flat substrate 24, 26 or alternatively, the ionization device 11 can be placed within a cylindrical channel, FIG. 2B.

The ionization device 11 of FIG. 2A includes a first electrode 14 placed within an insulating capillary tube 18 and a second electrode 16 wrapped around the capillary tube 18. The electrodes are separated by a gap G. One end of each of electrodes 14 and 16 is connected to the RF drive voltage supply 22 such that the electrodes function as the plates of a capacitor, separated by gap G, with the drive RF voltage applied across the two electrodes.

Figure 2B:
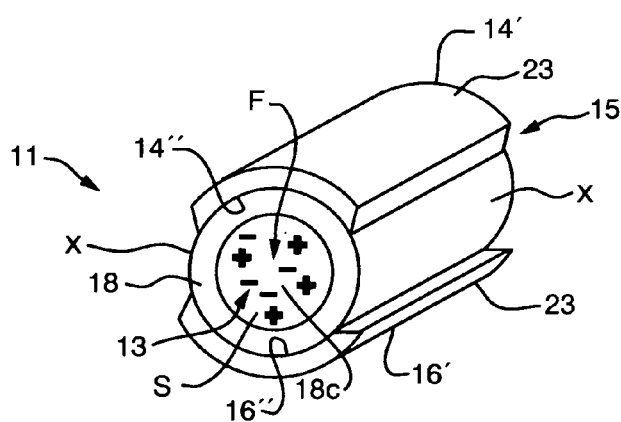

In a further embodiment of the invention, as shown in FIG. 2B, ionization device 11 includes an insulated substrate, such as glass capillary tube 18, coated with a metallization layer 23; this layer is parted at "x" to define two metallization regions forming electrodes 14', 16' of a plasma generator of the invention. The inner faces 14", 16" of these electrodes are formed on the insulating surfaces of the tube 18 and face each other through the tube 18 and across the open center 18c of the tube 18. It will be understood that an RF signal from source 22 is applied to these electrodes to generate field F within the tube 18.

In this embodiment, the gap separating the electrodes is defined by the diameter of the tube 18. Within the tube 18, the entire open center 18c may be utilized as an ionization region. In operation, the gas and sample S are flowed into the central passage 18c of the tube 18 through inlet 13. The carrier gas is ionized and forms a plasma field F which in turn ionizes the sample S between the electrodes 14, 16. Since the plasma has both positive and negative ions, the sample may be ionized into both positive and negative ions. The ions subsequently exit through outlet 15 for further use, such as in an ion mobility spectrometer.

In illustrative embodiments, such as shown in FIGS. 2A and 2B, the channel 12 has a diameter, $d_1$, of about 0.001-0.002 inches. The capillary tube 18 as a length, $l_1$, of about 0.01-0.05 inch, a diameter, $d_2$, of about 0.001-0.1 inches. The capillary tube 18 is made of quartz, glass or of any other suitable dielectric material. Electrodes 14 and 16 are typically made of gold, platinum, chromium, or any other suitable chemically passive conductive material.

Figure 2C:
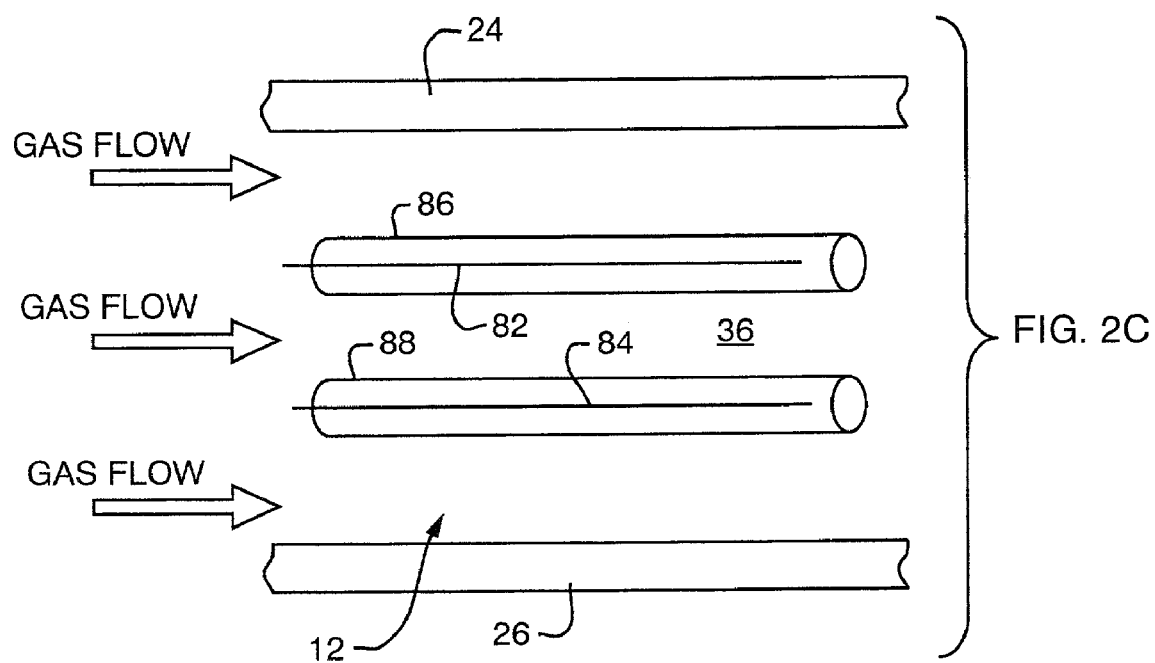

In further embodiments of the invention shown in FIGS. 2C and 2D, conducting electrodes 82, 84 are placed into tube-like dielectric sheaths 86, 88 (of glass, quartz, ceramic or other suitable material). Preferably these sheaths are fixtured so that the separation between the electrodes is fixed within ionization region 36. This separation can range from having the dielectric sheaths touching to having a separation of 5 mm or more.

It will be further observed that the electrodes 82, 84 in the embodiment of FIG. 2D are held and joined via collars 92, 94. Just beyond collar 94, the ionization region is effectively terminated as the electrodes begin to diverge. This arrangement enables defining the length of ionization region and thus avails predictable performance characteristics. Additionally, abutting collars 96, 98 are affixed on each of the tubes 86, 88 after collar 94 to fix this divergence. In various embodiments, the electrodes may be formed of conventional thin wire filaments and may be contained in a tube or coated with a dielectric or other insulating material.

The electrodes are separated by gap G, whether they are embedded in a dielectric material and mated or are within insulating tubes which abut. As will be appreciated by a person skilled in the art, the electrode diameter and dielectric coating material type and diameter are selected such that the fields generated between the electrodes are accessible to the gas flow. FIG. 2C is a simplified example, wherein the gas flows between the electrodes and therefore through the plasma-generating field between the electrodes. FIG. 2D is more difficult, wherein the air flows along the perimeter of the tubes and the field generated between the electrodes must extend into this peripheral flow. Therefore the applied signal, the filament and coating diameter all must be accommodate this external peripheral field F.

Figure 3:
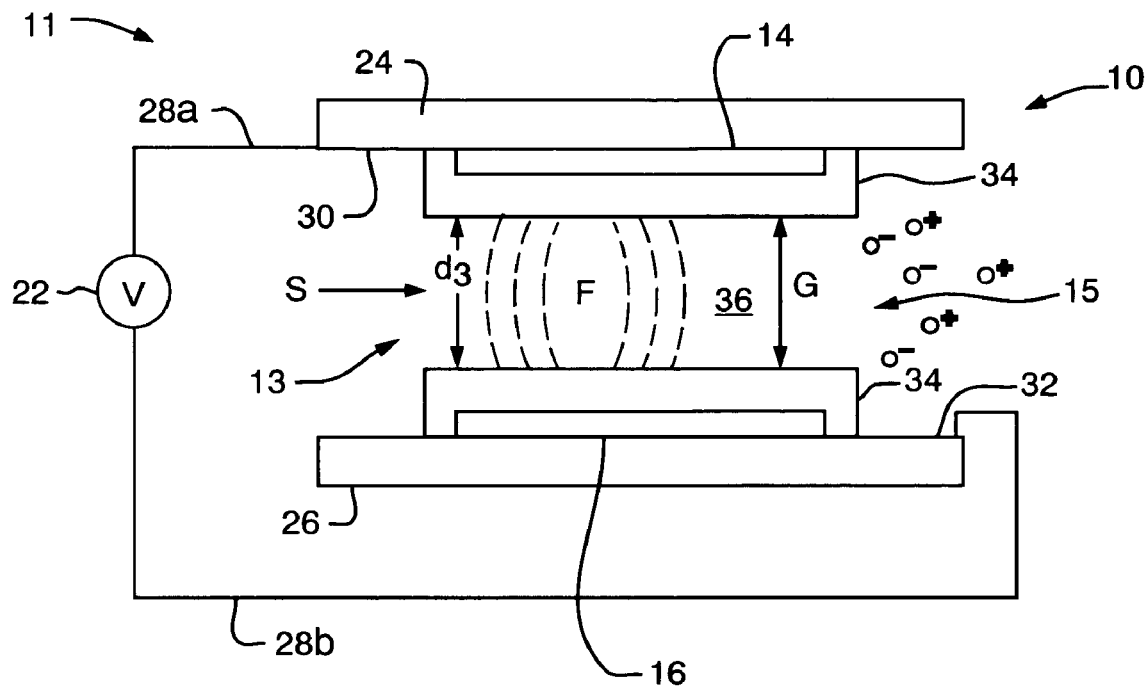
FIG. 3 is a planar embodiment of the capacitive discharge structure of the invention.

FIG. 3 is an alternative embodiment of the capacitive discharge structure of the invention, wherein ionization device 11 is configured as a planar apparatus 10. The first electrode 14 is a planar electrode on the underside of a first substrate 24, and the second electrode 16, also a planer electrode, is on top of a second substrate 26. The first electrode 14 and the second electrode 16 are connected via a pair of leads 28a, 28b to the same voltage supply 22, with respective conductive terminal pads 30 and 32.

Figure 4:
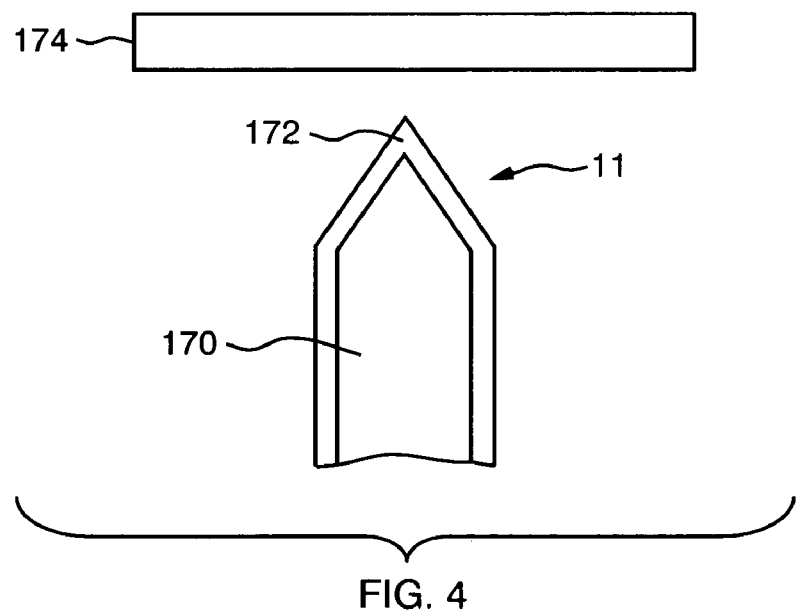
FIG. 4 is a needle electrode embodiment of the capacitive discharge structure of the invention.

In further practice of the embodiment of FIG. 3, an insulation layer 34 made of, for example, $Al_2O_3$ (Alumina) or $SiO_2$, or the like, is formed over one or both of electrodes 14, 16. In the embodiment shown in FIG. 3, the ionization device 11 is arranged with the opposing surfaces of the inner insulators 34 being spaced apart by a distance of $d_3$, of about 100 mm, defining gap G as ionization region 36. Furthermore, in the embodiment of the invention shown in FIG. 4, a needle electrode 170 is coated with insulator 172, and cooperates with a planar electrode 174 to form the plasma generator of the invention. Alternatively, the planar electrode 174 may be replaced with a second needle electrode.

It will be appreciated that although electrodes 14 and 16 are positioned parallel to each other in the device shown in FIG. 3, such a configuration is not necessary for the ionization device 10 to operate. Accordingly, the electrodes may be parallel or angled, flat or curved, within embodiments of the invention.

Figure 7:
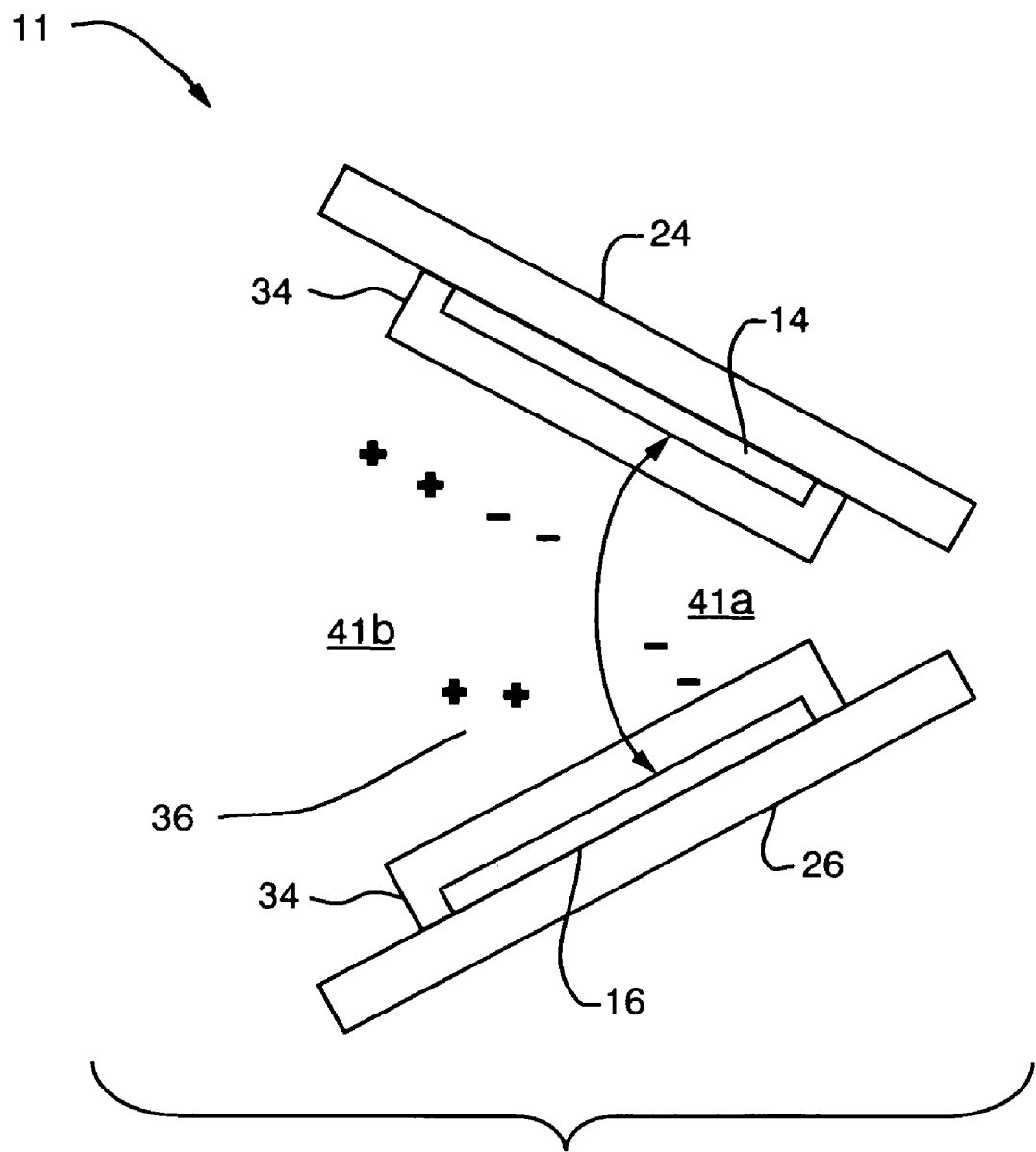
FIGS. 7-10 depict embodiments of the capacitive discharge plasma ionizer in practice of the invention.

In FIG. 7, electrodes 14, 16 are positioned at an angle so that the ionization region has a narrow region and a wide region. Electrodes 14, 16 are formed respectively on upper and lower substrates 24, 26, which are positioned at an angle, α. The angle, α, may be from about 10 degrees to about 90 degrees so that the ionization region 36 has a narrow region 41a and a wide region 41b. The gas that enters the ionization region is first ionized in the narrow region because the electrodes are closer together, which creates a higher field strength and hence a more intense ionization field. The electric field dissipates from the narrow region to the wide region the ionization process propagates from the narrow region to the wide region to generate the plasma (++,−−). Ionization of the sample now proceeds as earlier described.

Figure 8:
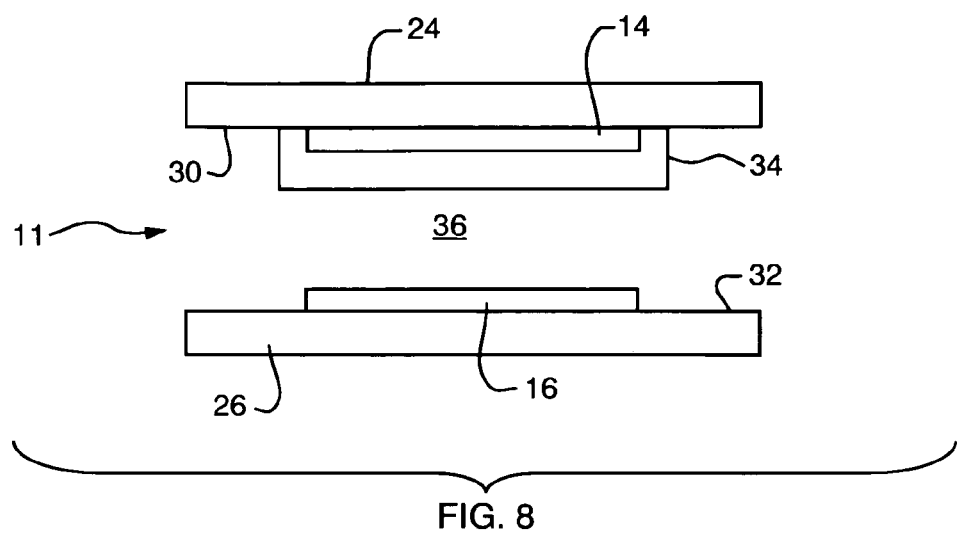

Up to now the planar electrodes 14 and 16 (FIGS. 3 and 7) have been shown with a respective inner insulator 34 that covers each of the electrodes. However, the plasma ionization device 11 of the invention is capable of functioning without the use of the inner insulator 34 on both electrodes. For example, in an alternative embodiment shown in FIG. 8, the second electrode 16 is not covered by an insulating material. Furthermore, the first electrode 14 need not be covered by the insulator. That is, both electrodes 14, 16 may be exposed directly to the sample gas.

Figure 9:
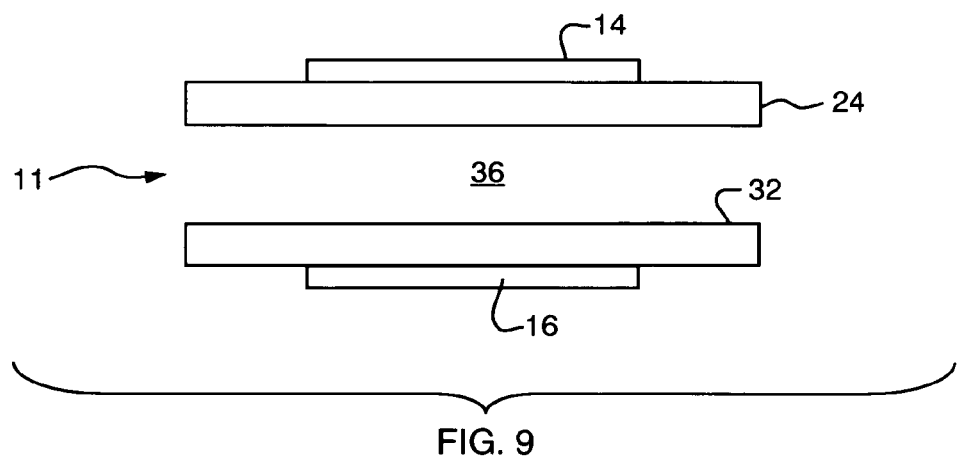
Figure 10:
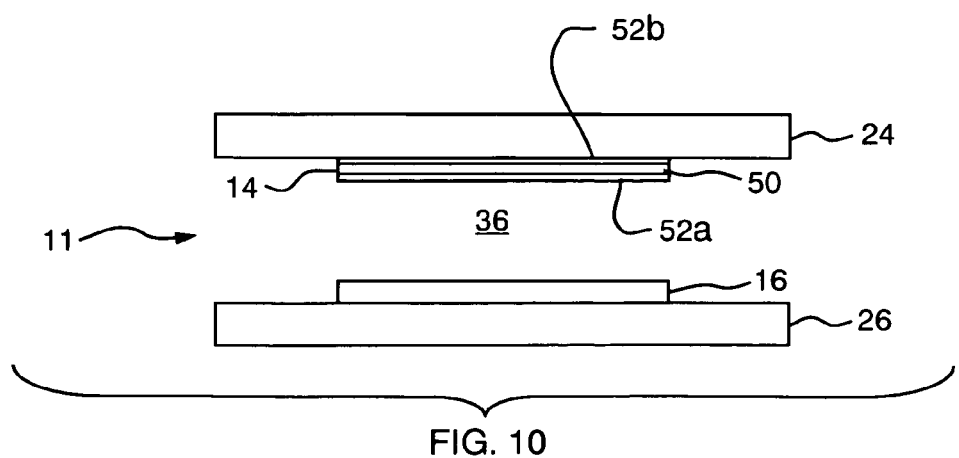

Alternatively, as shown in FIG. 9, electrodes 14 and 16 can be mounted to the respective outer surfaces of the substrates 24, 26. As evident in FIG. 9, neither electrode is covered by an insulating material. In yet another alternative embodiment illustrated in FIG. 10, electrode 16 is mounted to substrate 26, and electrode 14 is made of a dielectric substrate 50 coated with a metal layer 52a on one side of the dielectric substrate 50. The opposite side of the dielectric substrate 50 can also be coated with an additional metal layer 52b. In either case, electrode 14 is brazed to substrate 24 or attached with any other suitable attachment mechanism, such as, for example, epoxy glue.

Figure 11:
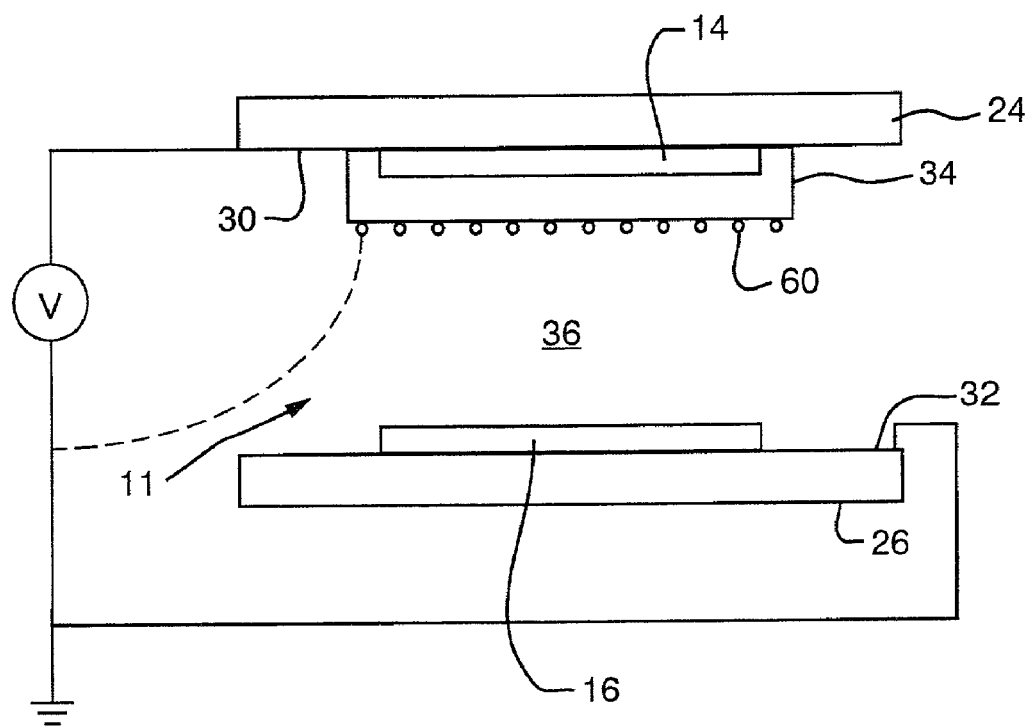
FIGS. 11 and 12 are schematics of alternative embodiments of capacitive discharge plasma ionizer of the invention with an accelerator electrode.
Figure 12:
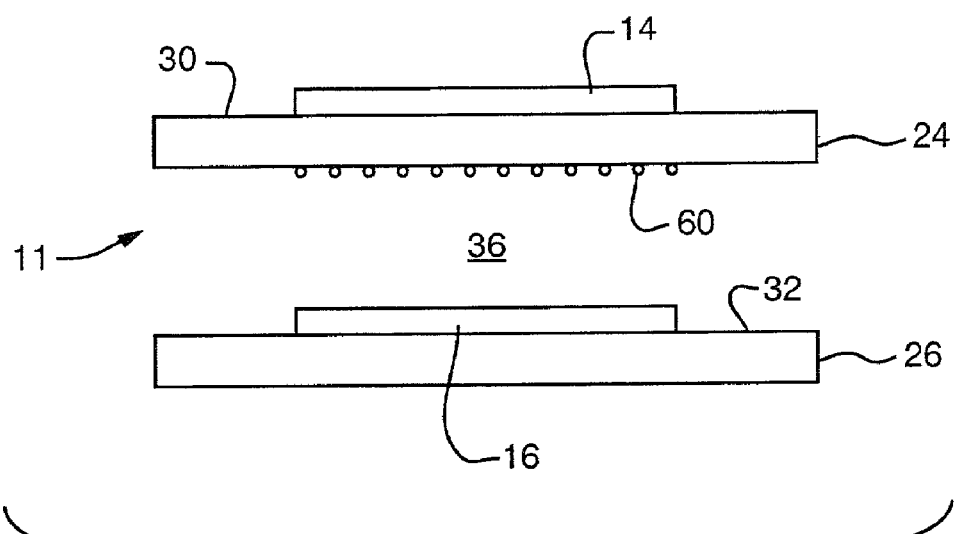

Referring now to FIG. 11, an alternative embodiment of the ionization device 11 includes an accelerator electrode 60, having its own self potential, mounted to the insulator layer 34 which covers electrode 14. Alternatively, electrode 14 and the accelerator electrode 60 can be mounted on opposite sides of substrate 24 as depicted in FIG. 12.

Figure 13A:
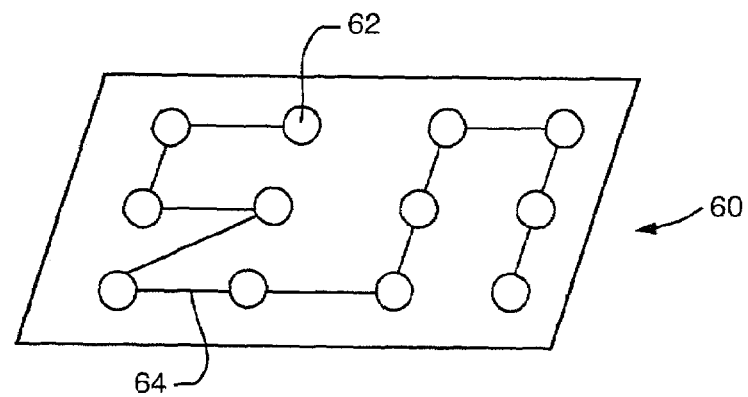
FIGS. 13A-C are alternative accelerator electrodes of the embodiments of FIGS. 11 and 12.
Figure 13B:
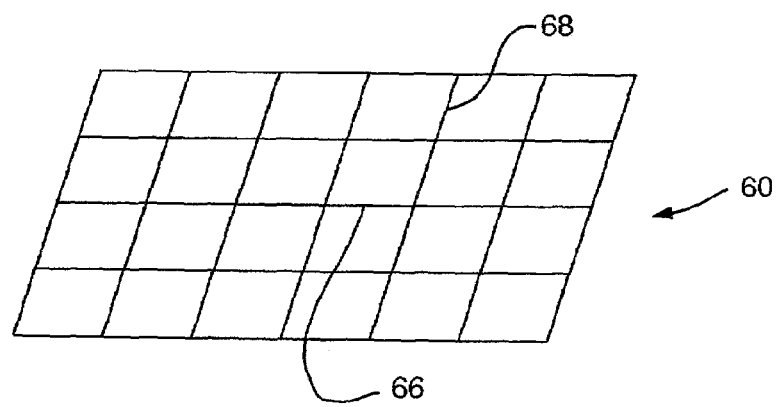
Figure 13C:
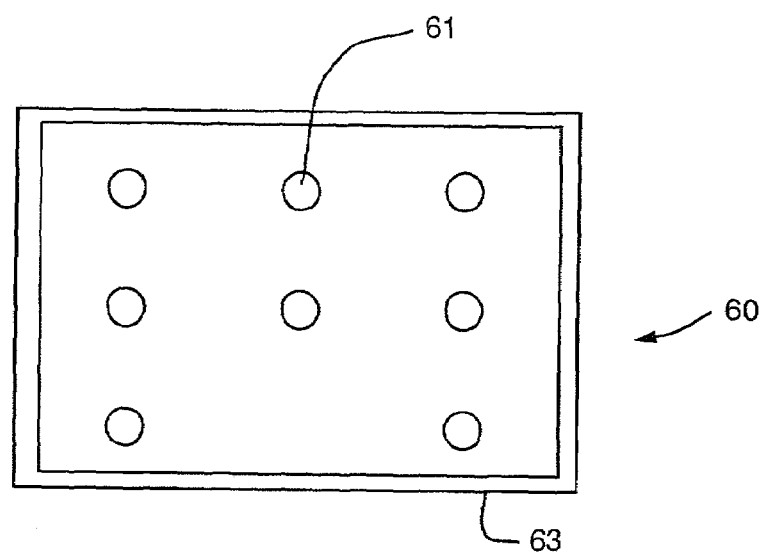

In either of the just described embodiments, the accelerator electrode 60 can be a series of small electrodes 62 interconnected with conductive wires 64, FIG. 13A, or a mesh of interconnected horizontal 66 and vertical 68 wires, for example, as shown in FIG. 13B. Alternatively, as shown in FIG. 13C, the accelerator electrode 60 can be an ensemble of small conductive electrodes 61 that are surrounded by a ring of conductive material 63, such as, for example, certain metals.

The various embodiments of the ionization device 11 discussed above are quite suitable for use in many types of gas analyzers and detectors. For example, there is shown in FIG. 14A a planar high field asymmetric waveform ion mobility spectrometer apparatus 70 which uses the ionization device 11 to generate ions for the chemical analysis of the sample S in the carrier gas CG.

The apparatus 70 includes the ionization devive 11, a filter 72 defining a filter region 74 between filter electrodes 76, 78, and a detector 80 defining a detection region 82 between detector electrodes 84, 86. Asymmetric field and compensation bias are applied to the filter electrodes 76, 78 by a drive circuit 88 within a control unit 90. The detector electrodes 84, 86 are also under the direction of the drive circuit 88 and control unit 90.

Briefly, in operation, the carrier gas, CG, is ionized in plasma region 36 forming plasma ions ++,−−, and the sample S in turn is ionized creating both positive and negative ionized molecules, $M^+$ and $M^-$. Based on FAIMS ion filtering techniques, only certain ion species pass through the filter region 74 while others are filtered out. Those that pass through are detected at detector electrodes 84, 86. Preferred configuration of apparatus 70 and its operation is described in greater detail in U.S. patent application Ser. No. 09/358,312, filed Jul. 21, 1999, the contents of which are incorporated herein by reference.

Figure 14A:
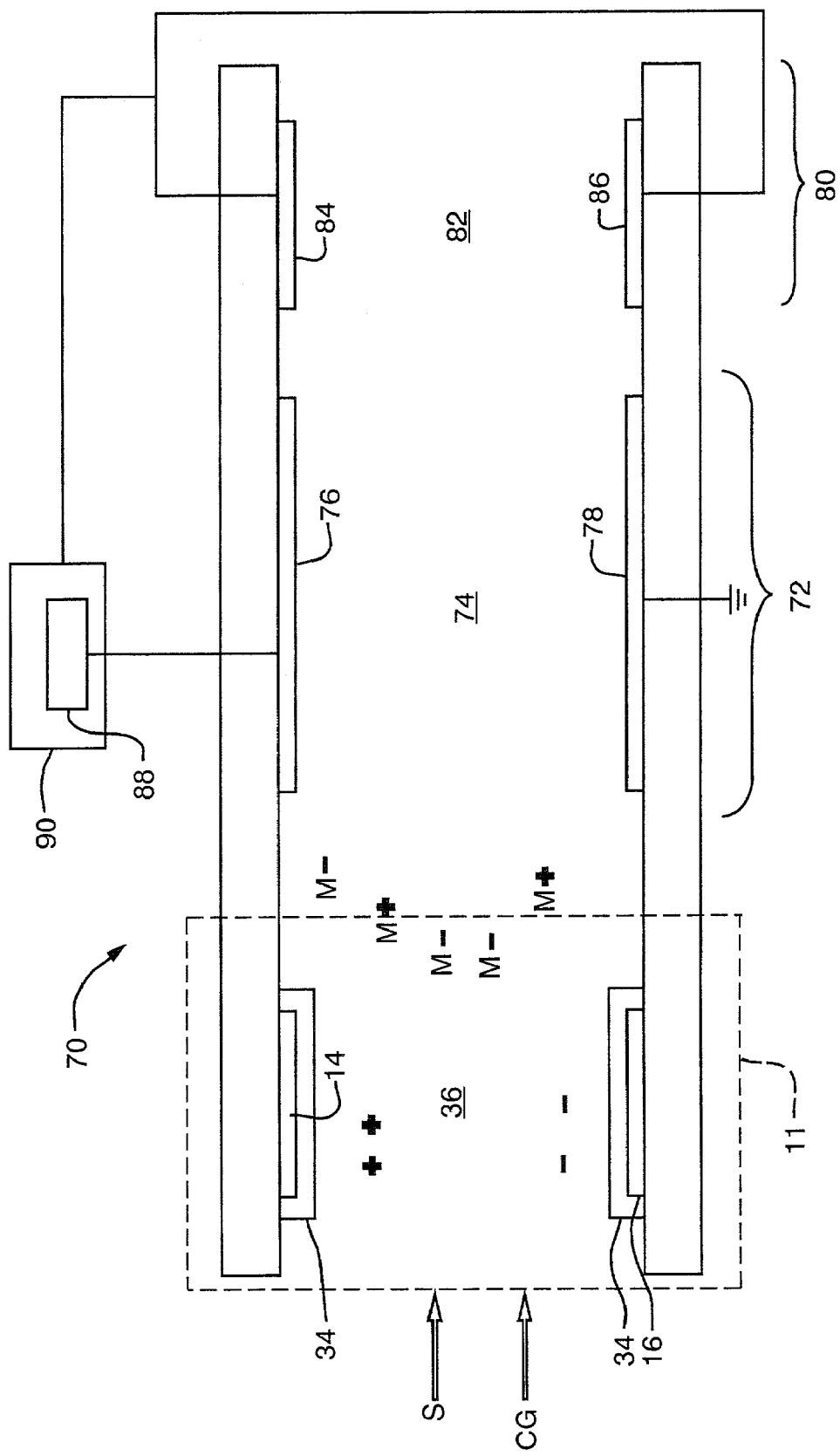
FIGS. 14A-D are schematics of alternative configurations of a planar high field asymmetric waveform ion mobility spectrometer incorporating an ionization device in practice of the invention.
Figure 14B:
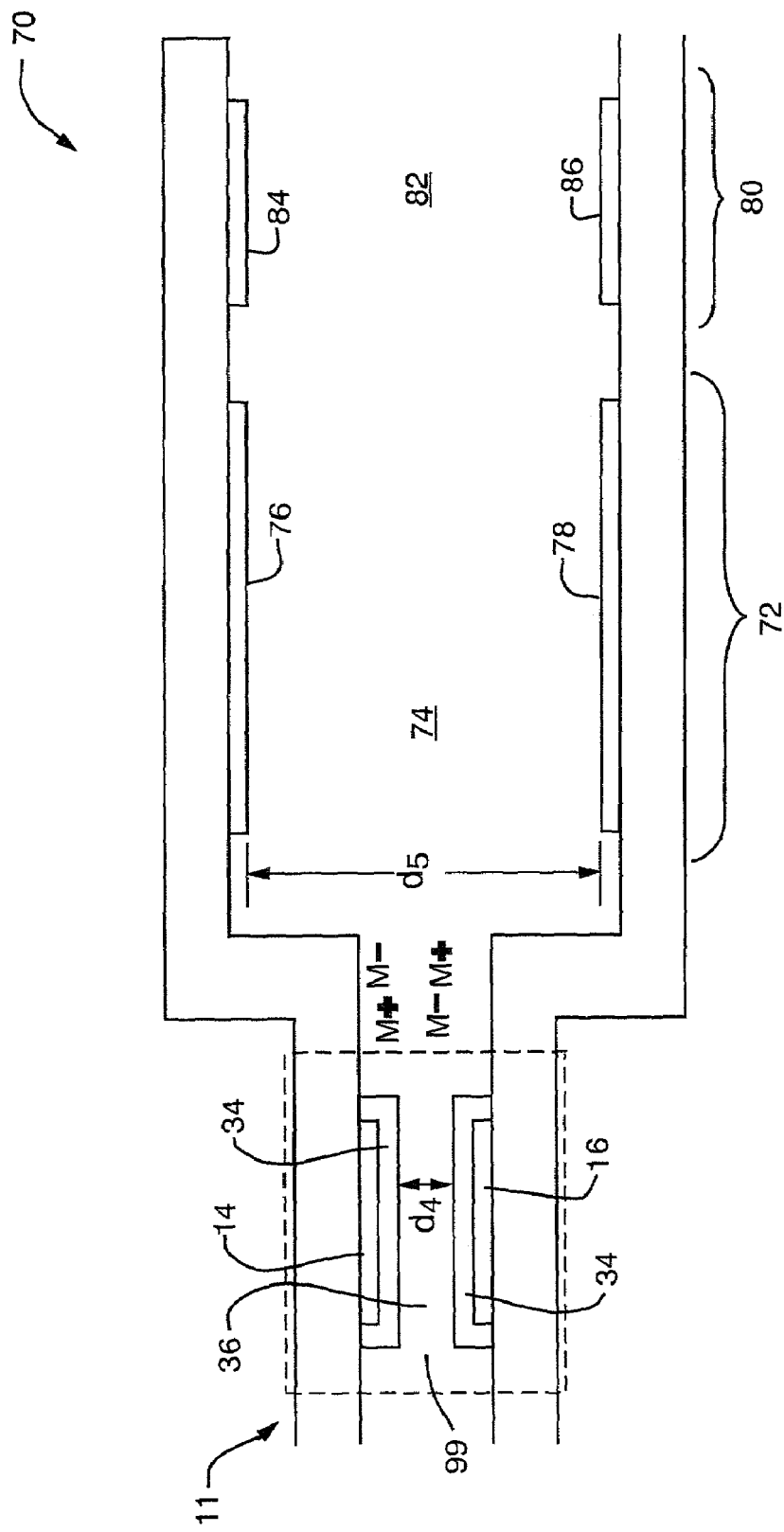

As depicted in FIG. 14A, electrodes 14, 76 and 84 are coplanar and electrodes 16, 78 and 86 are coplanar. Alternatively, as shown in FIG. 14B, apparatus 70 includes a necked down region 99 in which the ionization device 11 and electrodes 14, 16, resides. In this configuration, electrodes 14, 16 are spaced apart by a distance, $d_4$, of about 100 µm, while there is a distance, $d_5$, between the filter electrodes 76, 78.

Figure 14C:
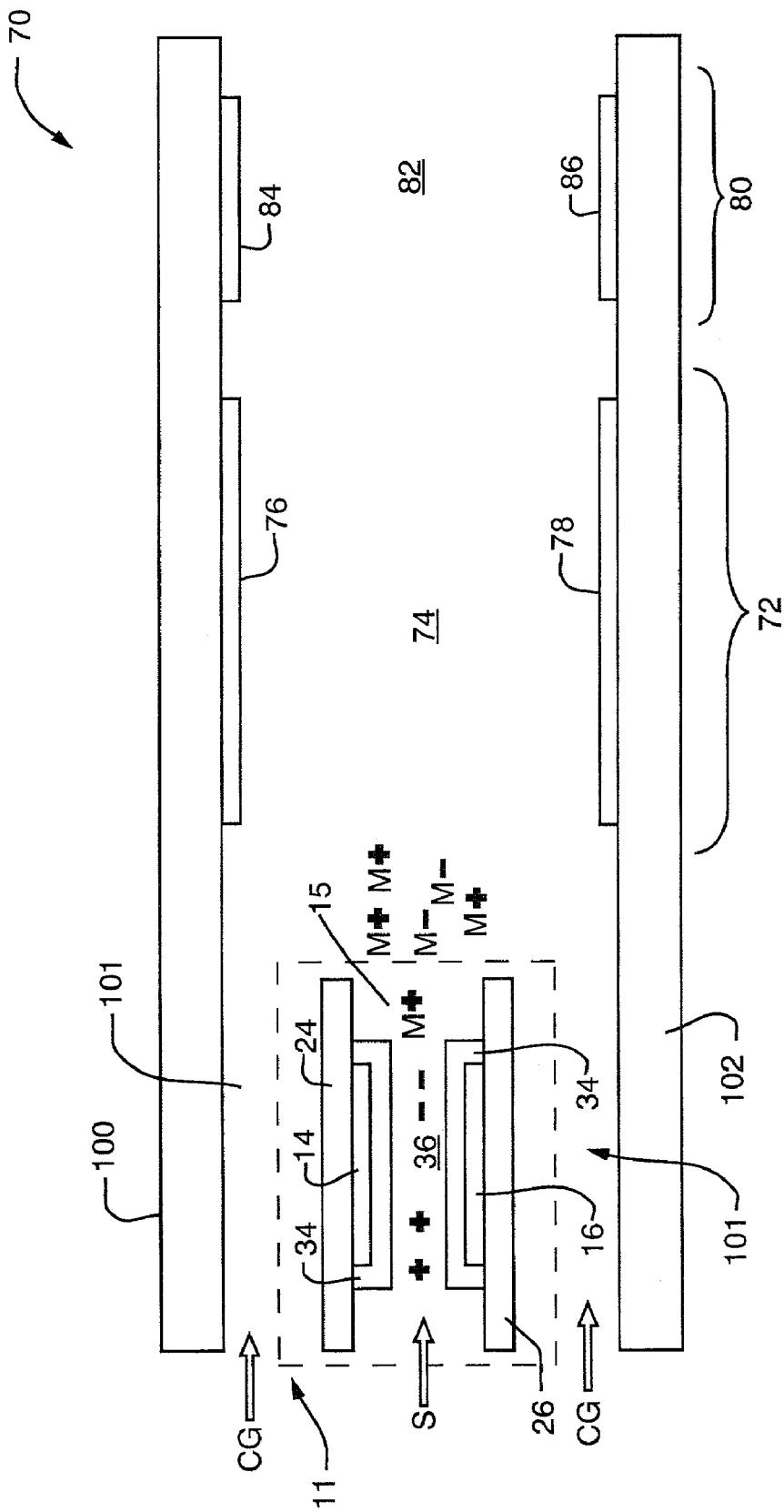

In yet another embodiment shown in FIG. 14C, the ionization device 11 is located within a channel 101 defined as outside a pair of substrates 100, 102. In such an arrangement, the carrier gas, CG, splits, and partly flows within the ionization region where it is ionized to form the plasma, ++,−−, and also over the outside of the ionization device 11 enclosed within the outer substrates 100, 102. The sample S then flows into the plasma ions ++,−− within the ionization region 36 and is ionized. The carrier gas now carries the ions from the outlet 15 of the ionization device 11 to the filter region 74 of the filter 72 for further analysis.

Figure 14D:
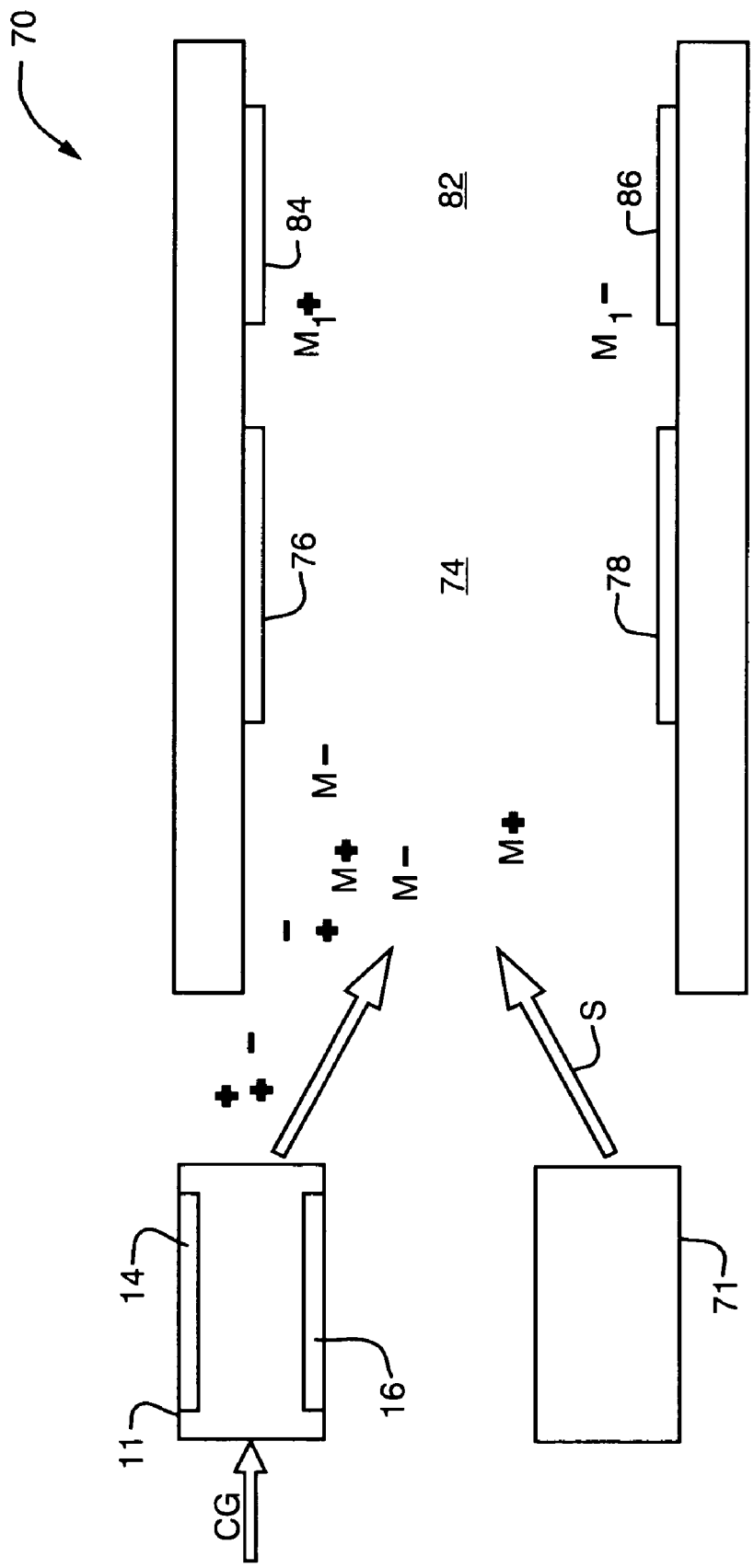

Referring now to FIG. 14D, there is shown another alternative embodiment of apparatus 70 that includes a sample source 71 which is separate from the ionization device 11. A gas, CG, is ionized to create ions, ++,−−, which in turn interact with and ionize sample S, before they flow into the filter region 74. With such a configuration, a variety of gases which are different from the sample gas can be mixed to create the ions.

In further embodiments the electrodes 14, 16 are positioned to create an intense ionization region, as an improvement of the embodiment of FIG. 7. For example, in the embodiment shown in FIG. 15A, a pair of ionization devices 11, 11 with non-parallel electrodes are employed in apparatus 70. The ionization devices 11, 11 are positioned within a channel 110 defined by an upper substrate 100, a lower substrate 102, a first spacer plate 104, and a second spacer plate 106, of plasma ionization apparatus 70. As the sample enters the ionization region 36, the ionization process initiates in the narrow regions 41a nearer each spacer plate and then progresses towards the wider regions 41b nearer the center of the channel 110.

Figure 15A:
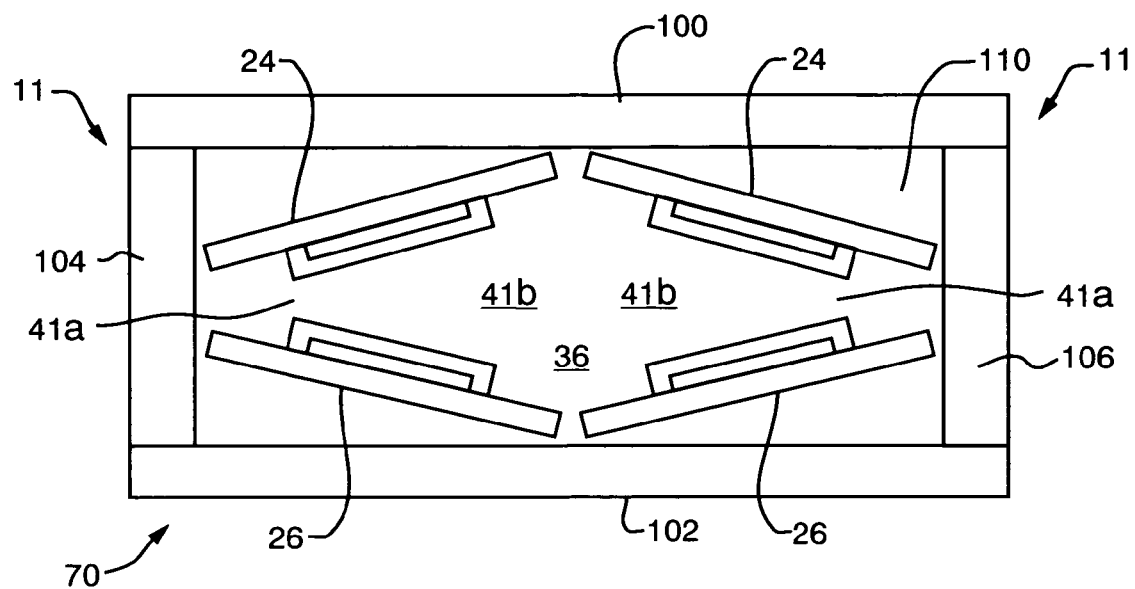
FIGS. 15A is an end view of a spectrometer apparatus with plasma ionization devices in practice of the invention.
Figure 15B:
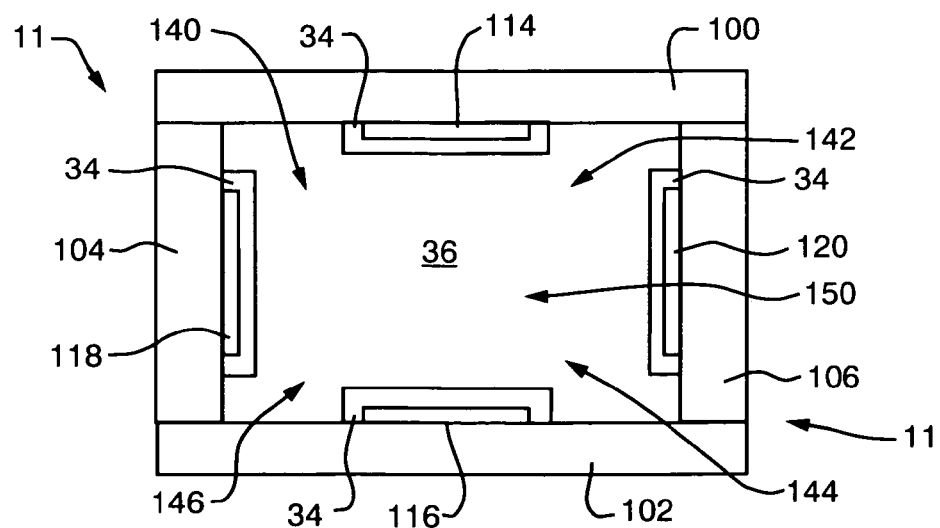
FIGS. 15B is an end view of a spectrometer apparatus with four electrodes arranged with each electrode positioned orthogonally to an adjacent electrode in practice of an alternative plasma ionization device of the invention.

These intense ionization regions can also be formed with the device illustrated in FIG. 15B which is conceptually an extension of the embodiment shown in FIG. 15A. Referring to FIG. 15B, the ionization device 11 includes a first electrode 114 mounted to an upper substrate 100, and a second electrode 116 mounted to an inner surface of a lower substrate 102. In addition, there is a third electrode 118 and a fourth electrode 120 mounted to the inner surfaces of side spacer substrates, 104, 106, respectively.

The electrodes 114, 116, 118, and 120 are coupled to a voltage source 22 (not shown) and are arranged with electrodes 114 and 118 forming the plates of one capacitor, and the electrodes 116 and 120 forming the plates of another capacitor, consistent with the invention. The electrodes 114 and 116 are of the same polarity, while the electrodes 116 and 120 are of the opposite polarity. With this configuration, there are four intense ionization regions 140, 142, 144, and 146 near the corners of the electrodes. When the gas enters the ionization region 36, the ionization process begins at these intense ionization regions and then propagates towards the center 150 of the ionization region 36 to form the desired plasma.

Figure 16:
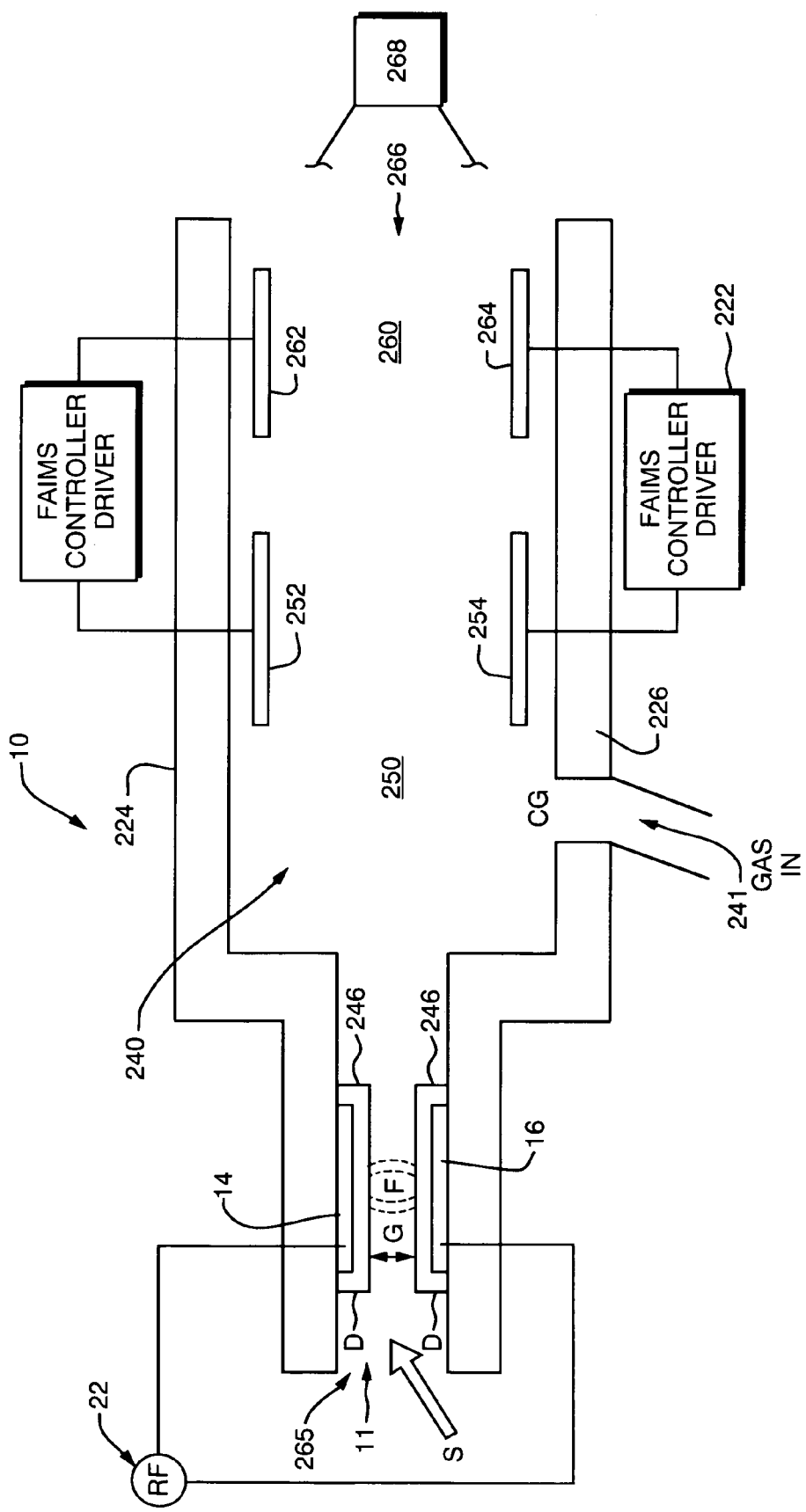
FIG. 16 is a system of the invention incorporating a capacitive discharge plasma ionization source for ionizing compounds in a chemical sample and having a FAIMS analyzer for receipt, analysis and identification of the ionized compounds.

FIG. 16 shows an alternative embodiment of the invention, wherein capacitive discharge ionization source 11 is integrated with a FAIMS apparatus in analytical system 10. The ionization device 11 is depicted with electrodes 14, 16 that produces the plasma of positively and negatively charged ions from high energy electric field F between the electrodes. In this embodiment, at least one and preferably two of the electrodes 14, 16 is coated with dielectric D. In alternative embodiments, the dielectric is mechanically distinct from the electrodes 14, 16, as opposed to a coating.

Continuing to refer to FIG. 16, system 10 further includes FAIMS apparatus 240, having filter 250 and detector 260 formed on substrates 238, 239. Filter 250 applies a compensated high field asymmetric waveform to a pair of filter electrodes 252, 254 that generate a high electric field therebetween. According to ion mobility characteristics of the ions passed into the filter field, a species of ions is passed for detection to a detector 260 which has a pair of detector electrodes 262, 264. In a typical FAIMS manner, the detection event is correlated with the applied drive voltages and known device performances to characterize the detected ion species, and now this can also be correlated with drive and control of the ionization device 11, for total analytical system control.

In operation, the carrier gas with a sample of chemical compounds are inputted at inlet 265 and the gas flows through the apparatus and out exhaust 266. Gas flow rate and pressure may also be controlled by use, for example, of a pump 268 associated with exhaust 266. The FAIMS system is driven and controlled by controller and driver circuit 222, which may be incorporated into and packaged with the plasma controller and drive circuit 22. Furthermore, the plasma generating electrodes 14, 16, filter electrodes 252, 254, and detector electrodes 262, 264 may all be separate and distinct structures or may be formed as electrodes on the surfaces of substrates, 238, 239, for example. The plasma-generating can be controlled and provides adequate energy to ionize compounds.

In the embodiment of FIG. 14C, the efficiency of ionization of the sample is increased by reducing the amount of carrier gas in the ionization region. In an alternative embodiment of the invention, also shown in FIG. 16, in order to increase the ratio of sample S to carrier gas, and thus to increase the efficiency of ionization of the sample, sample S is introduced with a minimized amount of carrier gas into ionization region. The carrier gas is ionized to form the plasma, which in turn ionizes the sample S, and then a second stream of carrier gas CG is introduced via an additional inlet 241 to carry the ions on for further analysis. Now a lower amount of background gas is ionized which relatively increases the ratio of sample to gas, thus improving ionization efficiency and reducing the REP in the analyzer.

Figure 17A:
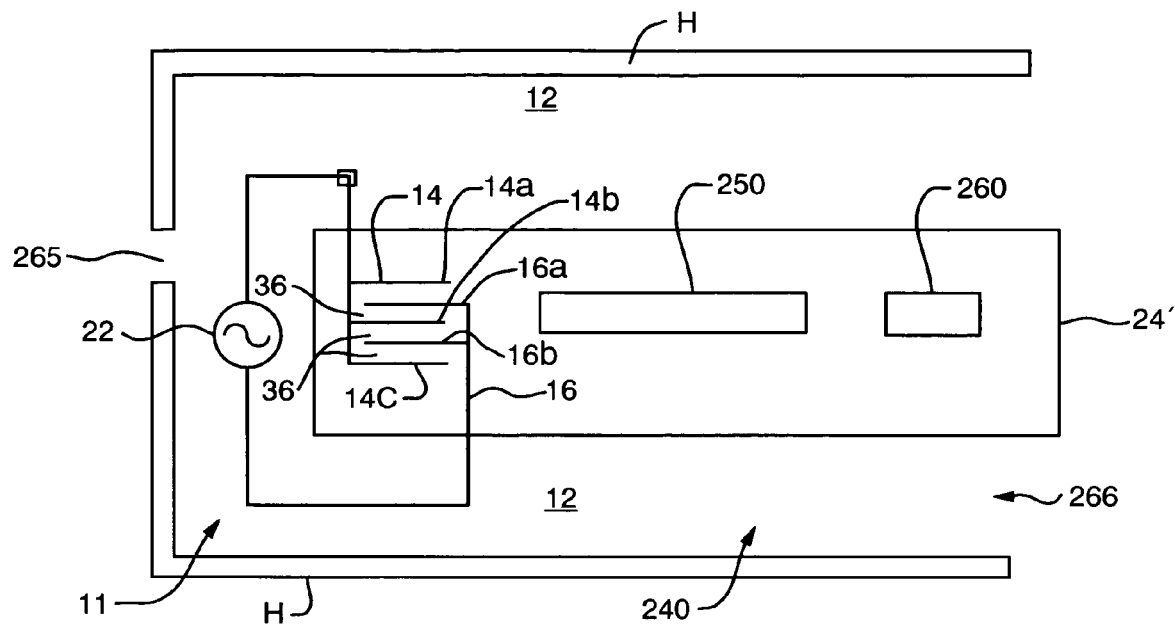
FIG. 17A shows intermeshed electrodes of a plasma generator formed on a single substrate in practice of the invention.
Figure 17B:
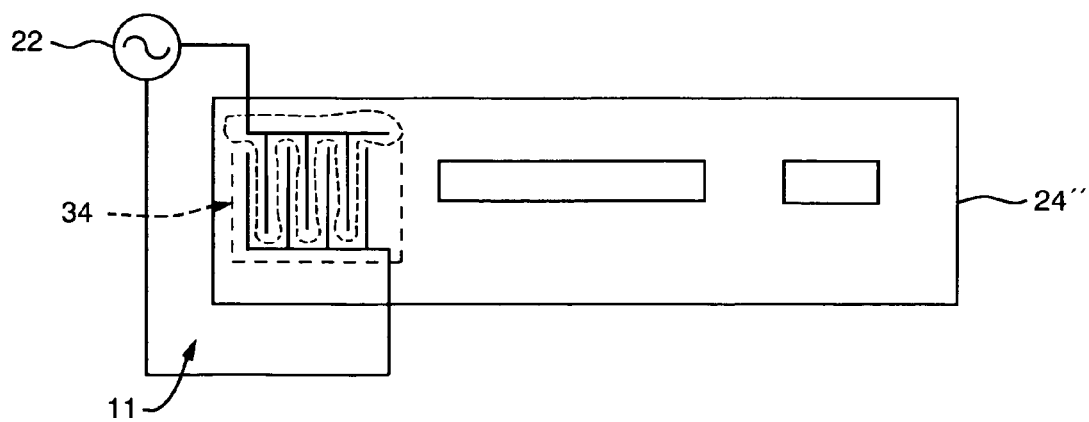
FIG. 17B shows an alternative embodiment rotated 90 degrees on the surface of the substrate.

Turning now to FIG. 17A, electrodes 14, 16 are formed on a single substrate 24'. The electrodes each extend to define a number of tines, such as tines 14a, 14b, 14c, 16a, 16b. These tines enable the electrodes to be intermeshed while forming plasma generator 11. Electrodes 14, 16 are driven by the RF source 22. FIG. 17B is similar but with the tine orientation rotated ninety degrees.

It will be appreciated that in a preferred embodiment, these electrodes are isolated from the gas flow. Such isolation is by use of an isolating or insulating layer, for example a dielectric coating 34 preferably formed on each exposed electrode (and tine) surface, such as, for example, $Al_2O_3$ (Alumina) or $SiO_2$, or the like, as indicated in FIG. 17B in dotted outline. (It will be further appreciated that various embodiments of the invention include use of isolation as earlier discussed and as shown in FIG. 17B and that this isolation is not shown in FIGS. 17A and 17C merely in order to ease presentation.)

The single substrate 24' may be enclosed in a flow channel 12 defined by a housing H to provide an entire plasma generator 11 of the invention, with sample intake at inlet 265 and exhaust at outlet 266.

Figure 17C:
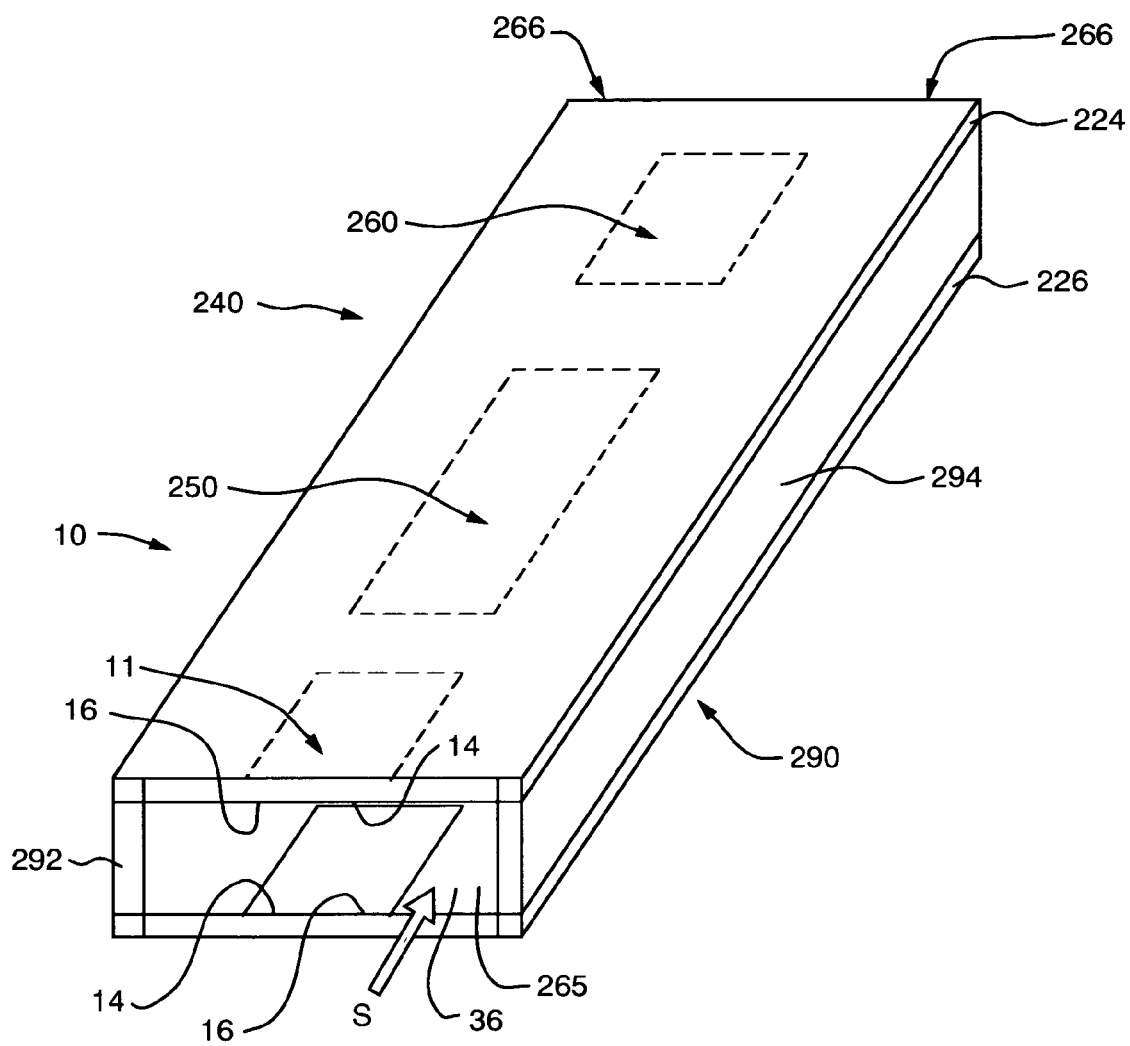
FIG. 17C is a microchip device with opposed substrates having a plurality of electrodes for plasma ionization and analysis according to the invention.

The plasma generator 11 of the invention may be formed on the same substrates that incorporate a FAIMS device. As shown in FIG. 17C, microchip 290 is formed incorporating a plasma generator 11 of the invention with identical or mating opposed substrates, 224, 226. In various embodiments, a separate plasma generator as in FIG. 17A may be formed on each of the facing substrate or one plasma generator may be formed by the opposed substrates, as in FIG. 16. A FAIMS device 240, having a filter 250 and optionally a detector 260 may also be defined within the same microchip structure 290.

Formation of a FAIMS device on mating substrates is disclosed in copending application Ser. No. 09/882,883, filed Jun. 15, 2001, entitled SPECTROMETER CHIP ASSEMBLY, incorporated herein by reference. Elongation of the leading or front end of such spectrometer chip assembly would accommodate formation of plasma generator 11 therein, such as now shown within microchip 290 in FIG. 17C.

In practice of embodiments of the invention, separation of the substrates and accurate spacing of the electrodes is desirable and may be achieved as needed, such as by use of spacer parts 292, 294 in the microchip structure 290, FIG. 17C. The substrates 224, 226 are formed mated against spacers 292, 294, which may be integral extensions of the substrates, or a housing, or separate components, as needed.

In the analytical system 10 shown in FIG. 17C, the carrier gas and sample S is introduced at inlet 265, and is ionized by the plasma process at generator 11. The ionized particles are analyzed in FAIMS device 240 (via FAIMS filter 250). The filter output may be directed to the input of a mass spectrometer or other detector device or simply to the input of an onboard detector 260, as shown, and then is exhausted at exit 266.

It will now be appreciated that the present invention relates to a novel, low-cost, non-radioactive, highly-efficient, clean and stable, radio frequency plasma ion source. It is capable of providing a wide range of plasma levels and is operable a low power over a range of pressures, including atmospheric pressure, in air. The invention is capable of ionizing a wide range of compounds, ranging from those having low ionization potential (such as acetone) to those having high ionization potential (such as $SF_6$), among various other compounds, for example.

It will be appreciated by a person skilled in the art that the present invention can be operated with control over formation of ions and ion species. As an illustration, the amount of energy in the plasma can be controlled, such as by control of the energy supplied by drive circuit 22. It will be appreciated that control of the amount of energy imparted into the gas and the resulting plasma controls the ion species generated in the plasma. By controlling this energy we can control formation of ions. Furthermore, this control may also be exercised to prevent formation of unwanted ions, such as nitrogen ions (NOx species), which can interfere with detection of other negative ions. It will be further appreciated by as person skilled in the art that adjusting gas flow rate can also be used to control the ion species that are formed in the plasma.

Based upon the foregoing discussion and illustrations, it will now be appreciated that plasma sources of the invention are useful in a wide range of systems that require sample ionization. The invention may be provided as a stand-alone device or may be incorporated into a larger system that can benefit from a clean and stable source of ions. Examples of such systems include FAIMS, ion mobility spectrometers, and atmospheric chemical pressure ionization spectrometers, among others. In fact, the present innovation has many practical applications, too numerous to illustrate herein.

It will now be appreciated that this invention has been particularly shown and described with reference to illustrative and preferred embodiments thereof. It will be understood by those skilled in the art that various changes in form and details may be made therein without departing from the spirit scope of the invention.

What is claimed is:

1. A method for capacitively providing a source of ions for an analytical system comprising,
    providing a flow through an electric field formed between two electrodes to form a plasma containing ionized molecules,
    inhibiting the plasma from contacting at least one of the electrodes, and
    passing the ionized molecules into an ion analyzer.

2. The method of claim 1, wherein the flow includes a gas.

3. The method of claim 1, wherein the flow includes air.

4. The method of claim 1 comprising generating the plasma at pressures including atmospheric pressure.

5. The method of claim 1 comprising generating the plasma to include both positive and negative ionized molecules.

6. The method of claim 1 comprising driving the electric field with a resonant circuit to form the plasma.

7. The method of claim 6 comprising including the two electrodes in the resonant circuit.

8. The method of claim 1 comprising driving the electric field with a sinusoidal wave form.

9. The method of claim 1 comprising driving the electric field with a pulsed waveform.

10. The method of claim 9, wherein the pulsed waveform includes packets of RF pulses.

11. The method of claim 10, wherein the RF pulses have a frequency between about 1 MHz and about 20 MHz.

12. The method of claim 10, wherein the packets have a duration of about 1 ms.

13. The method of claim 10, wherein the RF pulses have a peak-to-peak voltage of between about 1,000 volts and about 10,000 volts.

14. The method of claim 10, wherein the packets occur at a duty cycle of about 1:11 on.

15. The method of claim 1 comprising inhibiting the plasma from contacting both of the electrodes.

16. The method of claim 1, wherein the ion analyzer includes at least one of a mass spectrometer, an mobility based filter, an ion mobility spectrometer, a field asymmetric ion mobility spectrometer, and a time of flight spectrometer.

17. A capacitive discharge ion source for an analytical system comprising,
    first and second electrodes defining an ionization region and for forming an electric field therein,
    an inlet to the ionization region for providing a flow into the ionization region,
    a first isolator for inhibiting a plasma formed from ionizing the flow from contacting the first electrode, and
    an outlet to the ionization region for passing the flow to an ion analyzer.

18. The capacitive discharge ion source of claim 17, wherein the first isolator substantially covers the first electrode.

19. The capacitive discharge ion source of claim 18, wherein the dielectric material includes at least one of a ceramic, mica, glass, plastic, an oxide of a metal, a liquid, and a gas.

20. The capacitive discharge ion source of claim 17, wherein the first isolator is formed from a dielectric material.

21. The capacitive discharge ion source of claim 17 comprising a first substrate onto which the first electrode is mounted.

22. The capacitive discharge ion source of claim 21, wherein the first substrate includes a substantially planar surface and the first electrode is mounted onto the substantially planar surface.

23. The capacitive discharge ion source of claim 22 comprising a second substrate onto which the second electrode is mounted.

24. The capacitive discharge ion source of claim 23, wherein the second substrate includes a substantially planar surface and the second electrode is mounted on the substantially planar surface of the second substrate.

25. The capacitive discharge ion source of claim 23 comprising a second isolator for inhibiting the plasma formed from ionizing the flow from contacting the second electrode.

26. The capacitive discharge ion source of claim 17 comprising a drive circuit operatively coupled to the first and second electrodes for driving the electric field.

27. The capacitive discharge ion source of claim 26, wherein the drive circuit includes a resonant circuit.

28. The capacitive discharge ion source of claim 26, wherein the drive circuit is configured to drive the electric field with a sinusoidal wave form.

29. The capacitive discharge ion source of claim 26, wherein the drive circuit is configured to drive the electric field with a pulsed waveform.

30. The capacitive discharge ion source of claim 29, wherein the pulsed waveform includes packets of RF pulses.

31. The capacitive discharge ion source of claim 30, wherein the RF pulses have a frequency between about 1 MHz and about 20 MHz.

32. The capacitive discharge ion source of claim 30, wherein the packets have a duration of about 1 ms.

33. The capacitive discharge ion source of claim 30, wherein the RF pulses have a peak-to-peak voltage of between about 1,000 volts and about 10,000 volts.

34. The capacitive discharge ion source of claim 30, wherein the packets occur at a duty cycle of about 1:11 on.

35. The capacitive discharge ion source of claim 17 comprising a second isolator for inhibiting the plasma formed from ionizing the flow from contacting the second electrode.

36. The capacitive discharge ion source of claim 17, wherein the ion analyzer includes at least one of a mass spectrometer, an ion mobility based filter, an ion mobility spectrometer, a field asymmetric ion mobility spectrometer, and a time of flight spectrometer.

* * * * *